US012745953B2

(12) United States Patent
Pollonini et al.

(10) Patent No.: US 12,745,953 B2
(45) Date of Patent: Sep. 29, 2026

(54) SYSTEMS AND METHODS FOR DETECTION OF PRESSURE ULCERS

(71) Applicants: Scott E. Parzynski, Houston, TX (US); University of Houston System, Houston, TX (US); The Methodist Hospital, Houston, TX (US)

(72) Inventors: Luca Pollonini, Manvel, TX (US); Scott E. Parzynski, Houston, TX (US); Jeffrey D. Friedman, Houston, TX (US)

(73) Assignees: University of Houston System, Houston, TX (US); THE METHODIST HOSPITAL, Houston, TX (US); APOGEE INTERESTS, LLC, Houston, TX (US)

( * ) Notice: Subject to any disclaimer, the term of this patent is extended or adjusted under 35 U.S.C. 154(b) by 917 days.

(21) Appl. No.: 17/615,315

(22) PCT Filed: May 29, 2020

(86) PCT No.: PCT/US2020/035260
§ 371 (c)(1),
(2) Date: Nov. 30, 2021

(87) PCT Pub. No.: WO2020/243527
PCT Pub. Date: Dec. 3, 2020

(65) Prior Publication Data

US 2022/0218272 A1 Jul. 14, 2022

Related U.S. Application Data

(60) Provisional application No. 62/855,484, filed on May 31, 2019.

(51) Int. Cl.
*A61B 5/00* (2006.01)
*A61B 5/01* (2006.01)

(52) U.S. Cl.
CPC ............ *A61B 5/447* (2013.01); *A61B 5/0075* (2013.01); *A61B 5/015* (2013.01); *A61B 5/443* (2013.01);
(Continued)

(58) Field of Classification Search
CPC ....... A61B 5/447; A61B 5/0075; A61B 5/015; A61B 5/443; A61B 5/6833;
(Continued)

(56) References Cited

U.S. PATENT DOCUMENTS 8,116,838 B2 2/2012 Gaspard et al.
2003/0139667 A1 7/2003 Hewko et al.
(Continued)

FOREIGN PATENT DOCUMENTS

CZ 19 867 U1 10/2017
WO WO 2019/020666 1/2019

OTHER PUBLICATIONS

Examination Report for European Application No. 20813880.0 dated Jan. 25, 2024, 5 pages.
(Continued)

*Primary Examiner* — Abid A Mustansir
(74) *Attorney, Agent, or Firm* — pH IP Law

(57) ABSTRACT

Embodiments described herein generally relate to devices, methods and systems for determining differential blood oxygenation for early detection of pressure ulcers. By applying near infrared radiation of an appropriate wavelength to the tissue and determining the absorbance at a plurality of points where the distance between the source of the near infrared radiation and the detector are known, the oxygenation state of the hemoglobin can be determined based on position in a three-dimensional space.

23 Claims, 9 Drawing Sheets

(52) U.S. Cl.
CPC ...... *A61B 5/6833* (2013.01); *A61B 2562/029* (2013.01); *A61B 2562/046* (2013.01); *A61B 2562/164* (2013.01)

(58) Field of Classification Search
CPC ........ A61B 2562/029; A61B 2562/046; A61B 2562/164; A61B 5/1455; A61B 5/445
See application file for complete search history.

(56) References Cited

U.S. PATENT DOCUMENTS

| | | | | |
|---|---|---|---|---|
| 2005/0165284 | A1 | 7/2005 | Gefen | |
| 2011/0124987 | A1 | 5/2011 | Papazoglou et al. | |
| 2011/0208063 | A1 | 8/2011 | Papazoglou et al. | |
| 2015/0164347 | A1* | 6/2015 | Pollonini ............. | A61B 5/0261 600/323 |
| 2016/0022223 | A1 | 1/2016 | Grundfest et al. | |
| 2016/0296150 | A1 | 10/2016 | Kostic | |
| 2016/0296158 | A1 | 10/2016 | Papazoglou et al. | |
| 2017/0049380 | A1 | 2/2017 | Shachaf et al. | |
| 2017/0224271 | A1 | 8/2017 | Lachenbruch et al. | |
| 2017/0303830 | A1 | 10/2017 | Klein et al. | |
| 2019/0000328 | A1 | 1/2019 | Pollonini et al. | |
| 2019/0104982 | A1 | 4/2019 | Dunn et al. | |
| 2020/0015735 | A1* | 1/2020 | Burns .................... | A61B 5/445 |

OTHER PUBLICATIONS

Dehghani, H. et al., "Near infrared optical tomography using NIRFAST: Algorithm for numerical model and image reconstruction," *Commun Numer Methods Eng.*, 25.6 (2008): 711-732.

Extended European Search Report for EP Application No. 20813880.8dated Mar. 9, 2023, 9 pages.

Gefen, A., "The Future of Pressure Ulcer Prevention Is Here: Detecting and Targeting Inflammation Early," *EWMA Journal*, 19.2 (2018): 7-13.

Gould, L. J. et al., "Pressure ulcer summit 2018: An interdisciplinary approach to improve our understanding of the risk of pressure-induced tissue damage," *Wound Repair and Regeneration*, 27.5 (2019): 497-508.

Jayachandran, M. et al., "Critical Review of Noninvasive Optical Technologies for Wound Imaging," *Advances in Wound Care*, 5.8 (2016): 349-359.

Li, Z. et al., "Wavelet Analysis of Sacral Tissue Oxygenation Oscillations by Near-Infrared Spectroscopy in Persons with Spinal Cord Injury," *Microvascular Research*, 81.1 (2011): 81-87.

PCT International Preliminary Report on Patentability issued in International Patent Application No. PCT/US2020/035260, dated Dec. 9, 2021.

PCT International Search Report and Written Opinion issued in International Patent Application No. PCT/US2020/035260, dated Oct. 15, 2020.

Pollonini, L. et al., "Self-Contained Diffuse Optical Imaging System for Real-Time Detection and Localization of Vascular Occlusions," *Conf Proc IEEE Eng Med Biol Soc*, (2015): 5884-5887.

Pollonini, "UH Moment: Body Sensors", Houston Public Media, A Service of the University of Houston, Aug. 10, 2016, downloaded from the world wide web at houstonpublicmedia.org/articles/shows/uh-moment/2016/08/10/148083/uh-moment-body-sensors on May 24, 2023.

Redelings, M. D. et al., "Pressure Ulcers: More Lethal Than We Thought?," *Advances in Skin & Wound Care*, 18.7 (2005): 367-372.

Wang, Z. et al., "Image quality assessment: From error visibility to structural similarity," *IEEE Trans image Process*, 13.4 (2004): 600-612.

Zeff, B. W. et al., "Retinotopic mapping of adult human visual cortex with high-density diffuse optical tomography," *PNAS*, 104.29 (2007): 12169-12174.

Examination Report for European Application No. 20813880.0 dated Apr. 2, 2025, 4 pages.

Brief Communication issued in EP Application No. 20813880.8 dated May 15, 2026, 3 pages.

Machine Translation of CZ 19 867 U1, prepared on May 13, 2026.

* cited by examiner

SYSTEMS AND METHODS FOR DETECTION OF PRESSURE ULCERS

CROSS-REFERENCE TO RELATED APPLICATIONS

This application is a national phase application under 35 U.S.C. § 371 of International Application No. PCT/US2020/035260, filed May 29, 2020, which claims priority to U.S. Provisional Patent Application Ser. No. 62/855,484 filed May 31, 2019, the entire contents of each of which are incorporated by reference herein.

BACKGROUND

Field

Embodiments disclosed herein generally relate to systems and methods for detection of pressure ulcers, also known as pressure injuries (PIs). Particular embodiments relate to detection of pressure ulcers through changes in optical, temperature, humidity or other parameters. Pressure ulcers are wounds localized to the skin and/or underlying tissues that develop as a result of prolonged pressure exerted by a bony prominence (most frequently sacrum and heels) or a medical device. Although all populations with limited mobility are at risk of developing PIs, the highest rates are found in non-ambulatory patients who have no self-ability to reposition their body, especially those who are bed-bound recovering from trauma, surgery or acute illness in intensive care units (ICUs), terminally ill patients and wheelchair users. The prevention, assessment and treatment of PIs are universally considered part of nursing care, and since minimizing the pressure over bony prominences has long been considered the most effective method of PI prevention, patients at high risk of PIs need to be repositioned every two hours or less and receive a visual skin inspection by nursing staff to detect any newly developing PIs. Despite the recommended guidelines, the PI prevalence remains high (i.e., 2.5 million cases annually in the US alone, resulting in 60,000 deaths [1]).

Recent studies attribute the development of PIs to a series of cascading, additive and damaging events consisting of weight-related cell deformation damage, followed by an inflammatory response-related damage and culminated in an is-chemic damage [2]. These adverse events may originate within minutes of one another but then progress at different rates, cumulatively producing damage that propagates from the micro-scale (death of few cells) to the macro-scale (necrosis of tissue) within one to several hours. Despite the complexity of the PI pathogenesis, measuring tissue alterations in real-time may elucidate the origination mechanism and ultimately allow detecting PIs at the earliest stage.

Description of the Related Art

Pressure, or pressure in combination with friction, applied to a localized area of the body for an extended period of time results in significant alterations of blood flow and other physiological processes in the localized area, which in turn may originate a pressure ulcer (also known as a bed sore, decubitus ulcer or pressure injury, amongst other equivalent denominations). Common sites of development of pressure ulcers are in soft tissues over bony prominences, such as the sacrum, coccyx, heels, hips, elbows, knees, ankles, or the back of the shoulders and scalp. Pressure ulcers most commonly develop in individuals who are bedridden or confined to a wheelchair. Other factors—skin wetness such as sweating or incontinence, neuropathy, diabetes, infection, or arteriosclerosis—may influence the development of pressure ulcers. These factors can influence the tolerance of skin for pressure and shear.

There are currently four pressure ulcer stages from early tissue damage to severe damage. Stage I is marked by intact skin with non-blanchable redness with differing thicknesses and temperature as compared to adjacent tissue. Stage I ulcers are difficult to detect with the visible eye, especially in dark skinned individuals. Stage II is marked by partial thickness loss of the dermis with a pink wound bed or intact or open serum-filled blister. Stage III is marked by full thickness tissue loss resulting in exposure of subcutaneous fat. Stage IV is marked by full thickness tissue loss with exposed bone, tendon, or muscle. Healing time is prolonged and the percentage of recovery decreases for more advanced stage ulcers. Preventing pressure ulcers is challenging because the combination of pressure and time that results in tissue damage varies widely between patients. Pressure ulcers are currently detected by visual inspection performed periodically (i.e., every 2 hours). Although detecting a pressure ulcer at an early stage is critical to the patient's outcome, caregivers' busy schedule may prevent conducting skin observations often and, in certain kind of pressure-induced wounds such as deep tissue injuries (i.e., a pressure-induced injury that originates at the interface between tissue and bone and then propagate upwards to the skin), damage in tissues underlying the skin is often severe by the time a wound becomes visible superficially. Currently, no suitable devices or methods exist to detect early tissue damage that might enable intervention.

Thus, there is a need in the art for better monitoring of soft tissue in confined or immobile individuals for early detection of potential pressure ulcers.

SUMMARY

The embodiments described herein generally relate to methods, devices and systems for detection of pressure ulcers.

Briefly, this invention is based on the notion that monitoring in real time the effects of pressure and shear on tissues at risk by measuring various physiological parameters of interest such as blood perfusion, tissue oxygenation, tissue temperature and tissue moisture and optical parameters of interest such as tissue optical absorption, amongst others, and processing such information to predict an originating pressure ulcer at its earliest stage, allows to notify caregivers of such event for a timely intervention. This approach is enabled by a wearable sending patch able to measure the aforementioned parameters in real time and non-invasively. Preferably, blood perfusion, blood flow and tissue oxygenation information is measured optically using near infrared spectroscopy, whereas tissue (in particular, skin) moisture and temperature is measured with skin-contact electrical or optical sensing techniques, including but not limited to bio-impedance and infrared thermometry, respectively. Also preferably, a plurality of multimodal sensors are integrated in such a wearable sensing patch so that a superficial or volumetric map of blood-related parameters, heat and moisture can be created through proper processing of the sensed data, and ultimately detect the origination of a pressure ulcer by an automated analysis of such maps. Additionally, a single or a plurality of pressure sensors can be embedded in the wearable patch to quantify and map the amount of pressure applied to the skin.

In one embodiment, a multimodal imaging device comprises a near infrared spectroscopy device (NIRS) and temperature and INFO devices. The NIRS device includes a support with a first surface, a plurality of radiation sources positioned in connection with the first surface and a plurality of radiation detectors positioned in connection with the first surface. A temperature device includes a plurality of temperature detectors positioned in connection with the first surface, and a humidity device includes a plurality of humidity detectors positioned in connection with the first surface. The imaging device also includes a processor in connection with the NIRS device, temperature device and humidity device and a non-transitory memory adapted to store a plurality of machine-readable instructions. The instructions, when executed by the processor cause the imaging device to create a temperature map. The dimensions of the temperature map correspond to a thermal dispersion pattern. The instructions also cause the imaging device to create a humidity map. The humidity map corresponds to the amount of fluid vapor. The instructions also cause the imaging device to create a volumetric map of measured optical and physiological parameters. The volumetric map corresponds to the tissue portion. The instructions also cause the imaging device to subdivide the volumetric map into volumetric subregions. The volumetric subregions include a plurality of voxels with each voxel assigned one of preassigned value or random value. The instructions also cause the imaging device to create a sensitivity map based on a photon migration pattern. The instructions also cause the imaging device to overlay the sensitivity map onto the volumetric map. The instructions also cause the imaging device to perform at least one iterative cycle. The iterative cycle includes determining the measurement array and the calculated array for the volumetric map. The measurement array includes optical measurements corresponding to the photon migration pattern. The calculated array includes determining measurements corresponding to the assigned value as weighted by the photon migration pattern. The iterative cycle also includes increasing an assigned value of a test voxel of the volumetric map. Each test voxel is selected from the voxels of the volumetric subregions that will perturb the volumetric map. The iterative cycle includes calculating the perturbed determined measurements of the perturbed calculated array for the volumetric map and determining an error between the measurement array and the perturbed calculated array of the volumetric map. A transformation is applied locally to the test voxels and incorporates the error. The iterative cycle is repeated until one of a preset maximum is reached and the measurement error is less than a present threshold.

In one embodiment, a method for pressure ulcer detection is disclosed. The method includes positioning a near infrared spectroscopy device in connection with a tissue portion located on a body. The NIRS device is positioned for a near infrared measurement. The method further includes, collecting a first measurement using the NIRS device. The first measurement provides volumetric information regarding one of blood oxygenation and tissue perfusion. The method also includes comparing the first measurement to a threshold measurement to determine a change in one of blood oxygenation and tissue perfusion. The method further includes analyzing the change in one of blood oxygenation and tissue perfusion for pressure ulcer formation. The method also includes collecting a first temperature measurement using the NRS device. The first temperature measurement provides information regarding thermal dispersion. The method further includes analyzing the change in thermal dispersion for pressure ulcer formation Certain embodiments include a device comprising: a flexible support comprising a first surface, where the first surface is configured to be placed in proximity to an epidermis; and a radiation source coupled to the first surface of the support, where the radiation source is configured to emit a first emitted radiation signal at a first time period and a second emitted radiation signal at a second time period. In particular embodiments, the first emitted radiation signal and the second emitted radiation signal are emitted toward the epidermis when the first surface is placed in proximity to the epidermis; and the second time period is subsequent to the first time period. Exemplary embodiments include: a radiation detector coupled to the first surface of the support, where the radiation detector is configured to detect a first detected radiation signal at the first time period and a second detected radiation signal at the second time period; a processor in electronic communication with the radiation detector; and a non-transitory memory adapted to store a plurality of machine-readable instructions which, when executed by the processor, cause the device to: compare the first detected radiation signal to the second detected radiation signal to calculate a change in an optical property of the epidermis; and determine if the change in the optical property of the epidermis is indicative of a pressure ulcer.

In some embodiments, the radiation source is a first radiation source of a plurality of radiation sources. In specific embodiments, the radiation detector is a first radiation detector of a plurality of radiation detectors. In certain embodiments, the radiation source is configured to emit a continuous radiation signal that includes the first emitted radiation signal and the second emitted radiation signal. In particular embodiments, the second time period is between 1 second and 100 seconds after the first time period, or between 1 minute and 100 minutes after the first time period, or between 1 hour and 100 hours after the first time period, or between 1 day and 100 days after the first time period.

In some embodiments, the change in the optical property of the epidermis is a change in the optical density of the epidermis. In specific embodiments, the device may adjust the first or second emitted radiation signal or the first or second detected radiation signal to account for a pigmentation of the epidermis. In particular embodiments, the radiation detector is configured to detect a third detected radiation signal at a third time period; and the plurality of machine-readable instructions, when executed by the processor, cause the device to: compare the third detected radiation signal to the first detected radiation signal or the second detected radiation signal to calculate a change in an optical property of the epidermis; and determine if the change in the optical property of the epidermis is indicative of a pressure ulcer.

In specific embodiments, the radiation detector is configured to detect a fourth detected radiation signal at a fourth time period; and the plurality of machine-readable instructions, when executed by the processor, cause the device to: compare the fourth detected radiation signal to the first detected radiation signal, the second detected radiation signal, or the third detected radiation signal to calculate a change in an optical property of the epidermis; and determine if the change in the optical property of the epidermis is indicative of a pressure ulcer. In certain embodiments, the radiation detector is a component of a near infrared spectroscopy (NIRS) device. In particular embodiments, the change in the optical property of the epidermis is a value change in the optical density of the epidermis. In some embodiments, the change in the optical property of the epidermis is a change in the rate at which the optical density of the epidermis has changed.

Specific embodiments further comprise a temperature sensor, where: the temperature sensor is configured to obtain a first temperature reading at the first time period; the temperature sensor is configured to obtain a second temperature reading at the second time period; and the plurality of machine-readable instructions includes instructions which, when executed by the processor, cause the device to: compare the first temperature reading to the second temperature reading to calculate a change in a temperature of the epidermis; and determine if the change in the temperature of the epidermis is indicative of a pressure ulcer.

In certain embodiments, the change in the temperature of the epidermis is a value change in the temperature of the epidermis. In particular embodiments, the change in the temperature of the epidermis is a change in the rate at which the temperature of the epidermis has changed. Some embodiments further comprise a humidity sensor, where: the humidity sensor is configured to obtain a first humidity reading at the first time period; the humidity sensor is configured to obtain a second humidity reading at the second time period; and the plurality of machine-readable instructions includes instructions which, when executed by the processor, cause the device to: compare the first humidity reading to the second humidity reading to calculate a change in a humidity of the epidermis; and determine if the change in the humidity of the epidermis is indicative of a pressure ulcer.

In specific embodiments, the change in the humidity of the epidermis is a value change in the humidity of the epidermis. In certain embodiments, the change in the humidity of the epidermis is a change in the rate at which the humidity of the epidermis has changed. Particular embodiments further comprise: an optical detection device comprising a support comprising a first surface; where the radiation source is a first radiation source of a plurality of radiation sources positioned in connection with the first surface; where the radiation detector is a first radiation detector of a plurality of radiation detectors positioned in connection with the first surface. Exemplary embodiments also comprise: a processor in connection with the optical detection device; and a non-transitory memory adapted to store a plurality of machine-readable instructions which, when executed by the processor, cause the device to: create a volumetric map, the dimensions of the volumetric map corresponding to the tissue portion; subdivide the volumetric map into volumetric subregions, the volumetric subregions comprising a plurality of voxels, each voxel being assigned one of preassigned values and random values; create a sensitivity map based on a photon migration pattern; overlay the sensitivity map onto the volumetric map; and perform at least one iterative cycle, the iterative cycle comprising: determining the measurement array and the calculated array for the volumetric map, the measurement array comprising optical measurements corresponding to the photon migration pattern, the calculated array comprising determined measurements corresponding to the assigned value as weighted by the photon migration pattern; increasing an assigned value of a test voxel of the volumetric map, each of the test voxel being selected from the voxels of the volumetric subregions, the increase perturbing the volumetric map; calculating perturbed determined measurements of a perturbed calculated array for the volumetric map; and determining an error between the measurement array and the perturbed calculated array of the volumetric map, wherein a transformation is applied locally to the test voxel and incorporates the error; and repeat the iterative cycle until one of a preset maximum is reached and the measurement error is less than a present threshold.

In some embodiments, the optical device is a near infrared spectroscopy (NIRS) device. In specific embodiments, the device further comprises: a plurality of temperature detectors positioned in connection with the first surface; and the plurality of machine-readable instructions includes instructions which, when executed by the processor, cause the device to create a temperature map, the dimensions of the temperature map corresponding to a thermal dispersion pattern.

In certain embodiments, the device further comprises: a plurality of humidity detectors positioned in connection with the first surface; the plurality of machine-readable instructions includes instructions which, when executed by the processor, cause the device to create a humidity map, the dimensions of the humidity map corresponding to a fluid vapor amount. In particular embodiments, each voxel is assigned a value determined by a previous set of iterative cycle. In some embodiments, the plurality of radiation sources are positioned equidistance from the detector.

In specific embodiments, the transformation comprises a volumetric Gaussian kernel, wherein if the perturbation causes the error to go down, then the volumetric Gaussian kernel having a radius is centered on the test voxel, the volumetric Gaussian kernel extending to a plurality of proximate voxels, the test voxel and the proximate voxels being permanently increased in value proportionally to the magnitude of the error decrease multiplied by a proportional factor A, and if the perturbation causes the error to go up, then a volumetric Gaussian kernel having a radius is centered on the test voxel, the volumetric Gaussian kernel extending to a plurality of proximate voxels, the test voxel and the proximate voxels being permanently decreased in value proportionally to the magnitude of the error increase multiplied by a proportional factor A.

In certain embodiments, at least one of the plurality of radiation sources delivers radiation at a wavelength of about 660 nm. In particular embodiments, at least one of the plurality of radiation sources delivers radiation at a wavelength of about 880 nm. In some embodiments, the support has an octagonal shape and the radiation sources are configured in concentric circles expanding from a detector in the center of the octagonal shape.

Certain embodiments include a method for pressure ulcer detection, sequentially comprising: positioning a near infrared spectroscopy (NIRS) device in connection with a tissue portion located on a body, the NIRS device being positioned for a near infrared measurement; collecting a first measurement using the NIRS device, the first measurement providing volumetric information regarding one of blood oxygenation and tissue perfusion; comparing the first measurement to a threshold measurement to determine a change in one of blood oxygenation and tissue perfusion; and analyzing the change in one of blood oxygenation and tissue perfusion for pressure ulcer formation.

In particular embodiments, the threshold measurement is a prior measurement obtained by the NIRS device. In some embodiments, the tissue portion is disposed on the exterior of and underneath the body. In specific embodiments, the NIRS device comprises a plurality of first radiation sources, a plurality of second radiation sources and a plurality of detectors connected to a support. In certain embodiments, the NIRS device comprises a plurality of humidity sensors and a plurality of temperature sensors. In particular embodiments, the first radiation sources each deliver a first radiation, and wherein the first radiation is a radiation with a wavelength between 650 nm and 800 nm. In some embodiments, the second radiation sources each deliver a second radiation, wherein the second radiation is a radiation with a wavelength between 800 nm and 1000 nm. In specific embodiments, a first measurement and a second measurement are selected samples from a continuous measurement.

Certain embodiments include a method for pressure ulcer detection, sequentially comprising: positioning a near infrared spectroscopy (NIRS) device in connection with a tissue portion located on a body, the NIRS device being positioned for a near infrared measurement; collecting a first measurement using the NIRS device, the first measurement providing volumetric information regarding blood oxygenation or tissue perfusion; comparing the first measurement to a threshold measurement to determine a change in one of blood oxygenation and tissue perfusion; analyzing the change in one of blood oxygenation and tissue perfusion for pressure ulcer formation; collecting a first temperature measurement using the NRS device, the first temperature measurement providing information regarding thermal dispersion; and analyzing the change in thermal dispersion for pressure ulcer formation.

Particular embodiments further comprise collecting a first humidity measurement using the NIRS device, the first humidity measurement providing information regarding fluid vapor quantity. In some embodiments, the NIRS device comprises a plurality of first radiation sources, a plurality of second radiation sources and a plurality of detectors connected to a support. In specific embodiments, the NIRS device comprises a plurality of humidity sensors and a plurality of temperature sensors. In certain embodiments, the first radiation sources each deliver a first radiation, and wherein the first radiation is a radiation with a wavelength between 650 nm and 800 nm. In particular embodiments, the second radiation sources each deliver a second radiation, wherein the second radiation is a radiation with a wavelength between 800 nm and 1000 nm.

BRIEF DESCRIPTION OF THE DRAWINGS

So that the manner in which the above recited features of the present inventions can be understood in detail, a more particular description of the inventions, briefly summarized above, may be had by reference to embodiments, some of which are illustrated in the appended drawings. It is to be noted, however, that the appended drawings illustrate only typical embodiments of this inventions and are therefore not to be considered limiting of its scope, for the inventions may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments disclosed herein generally relate to systems and methods for detection of pressure ulcers. Particular embodiments relate to detection of pressure ulcers through changes in optical, temperature, humidity or other parameters.

Figure 1:
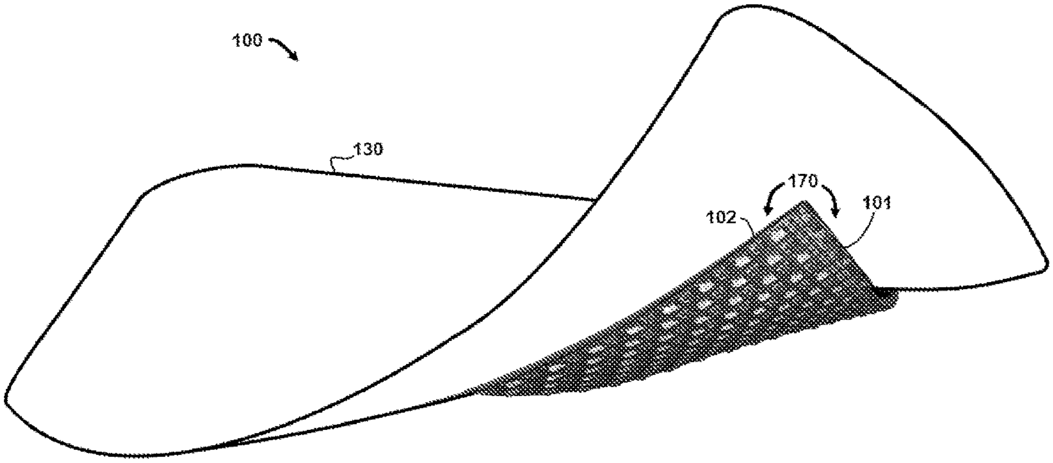
FIG. 1 depicts a perspective view of a device according to an embodiment disclosed herein.
Figure 2:
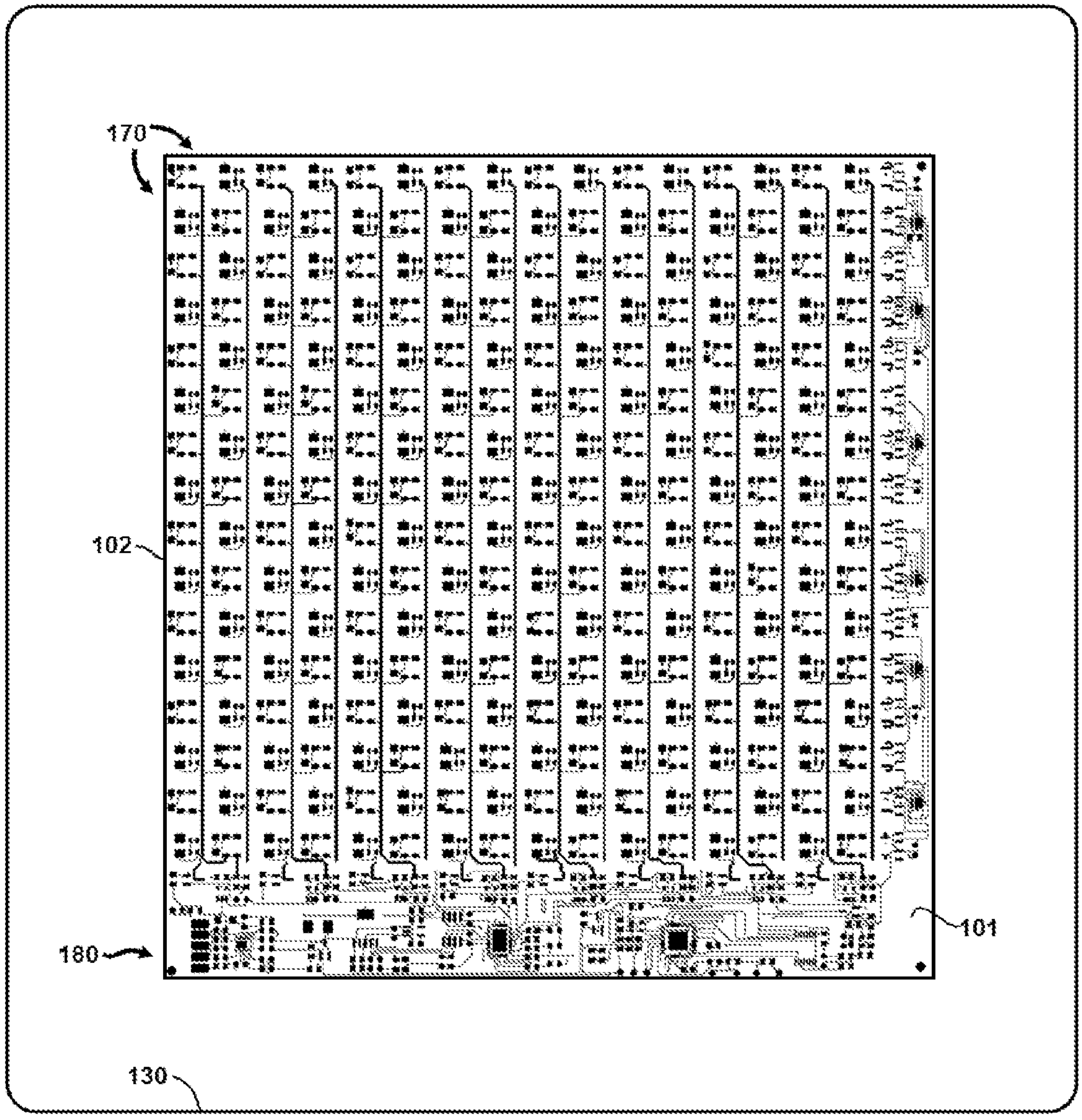
FIG. 2 depicts a bottom view of a device according to an embodiment disclosed herein.

Referring initially to FIG. 1 and FIG. 2, a device 100 is depicted according to an exemplary embodiment of the present disclosure. As discussed further below, device 100 comprises a support 102 in connection with a plurality of sensors 170 configured to detect conditions that can indicate potential formation of a pressure ulcer. Device 100 also comprises electronic components 180 (e.g. processors, communication modules, etc.) configured to allow sensors 170 to communicate with a data collection unit 135 (shown and discussed below in FIG. 6). While FIG. 1 and FIG. 2 illustrate an embodiment with a large array of sensors 170, it is understood that other embodiments may comprise a smaller number of sensors than those shown in the figures. For example, certain embodiments may comprise a single sensor, or a single pair of sensors.

In the embodiment shown, device 100 comprises a casing 130 and support 102 that are flexible and can accommodate the complex curvatures associated with regions of interest on a patient (human or animal) in which a pressure ulcer may form. Such regions may include, for example the sacral region of the patient. In exemplary embodiments, casing 130 and support 102 are also flexible enough to conform to a bony prominence, including for example, an elbow, spine, hip, heel, knee or ankle. In particular embodiments, casing 130 may comprise an adhesive configured to couple device 100 to the surface of the subject's skin. In certain embodiments, casing 130 may comprise a pad or cushion (e.g. a foam bandage) that extends around support 102 to avoid creating additional pressure points on the subject at the location of device 100.

In the illustrated embodiment, sensors 170 are coupled to a first surface 101 of support 102. During use, first surface 101 can be placed in proximity to an epidermis such that sensors 170 can detect physiological conditions that can indicate a pressure ulcer may be forming in the region of the epidermis covered by device 100. In a particular embodiment, sensors 170 may comprise a radiation source and a radiation detector coupled to the first surface 101 of support 102. In certain embodiments, the radiation detector is a near infrared spectroscopy (NIRS) device.

During use of device 100, the radiation source can emit radiation signals toward the epidermis over subsequent time periods and the radiation detector can detect radiation signals in response to the emitted signals. Electronic components 180 can also comprise a processor that compares the detected radiation signals to calculate a change in an optical property (e.g. the optical density) of the layers of skin tissue. In addition, the processor can determine if the change in the optical property of the epidermis and underlying tissue is indicative of a pressure ulcer. In certain embodiments, device 100 may adjust (e.g. increase or decrease) the signal emitted from a radiation source and/or the signal detected by a radiation detector to account for different skin pigmentations. For nomenclature purposes, this disclosure refers to a first radiation signal emitted or detected at a first time period and a second radiation signal emitted or detected at a second time period. It is understood that in exemplary embodiments, a continuous radiation signal emitted or detected at two different time periods includes a first radiation signal emitted or detected at a first time period and a second radiation signal emitted or detected at a second time period. In addition, the length of time between the first time period may be seconds, minutes, hours or days in certain embodiments.

In exemplary embodiments, sensors 170 can comprise optical detectors, temperature sensors, and/or humidity sensors. It is understood that certain embodiments may comprise any combination of the different types of sensors disclosed herein. In particular embodiments, device 100 may detect changes in optical, temperature or humidity conditions over time for a specific location. In certain embodiments, one or more temperature sensors can obtain a first temperature reading at a first time period and obtain a second temperature reading at a second subsequent time period. The processor can then compare the first temperature reading or readings to the second temperature reading or readings to calculate a change in a temperature of the epidermis and determine if the change in the temperature of the epidermis is indicative of a pressure ulcer.

Particular embodiments can also include one or more humidity sensors that can obtain a first humidity reading at a first time period and obtain a humidity reading at a second subsequent time period. The processor can then compare the first humidity reading or readings to the second humidity reading or readings to calculate a change in a humidity of the epidermis and determine if the change in the humidity of the epidermis is indicative of a pressure ulcer. In particular embodiments, the processor can execute an algorithm that analyzes data relating to optical, thermal and/or humidity conditions (or any combination of the different types of data) to determine if the conditions are indicative of a pressure ulcer. In particular embodiments, an increase in temperature and humidity accompanied with a decrease in optical density can indicate conditions are conducive to forming a pressure ulcer. In certain embodiments, the processor can execute an algorithm that calculates changes in absolute data and/or calculates rates of changes of the data obtained by sensors 170 to determine if a pressure ulcer is likely to form.

Device 100 can be affixed to a subject in a specific location and remain at the location to monitor conditions over a period of time. As the optical, temperature or humidity conditions change during the monitored time period, an indicator or alert can be provided that a potential pressure ulcer may be forming in the region monitored by device 100. If it is desired to monitor multiple regions, then multiple devices 100 can be affixed to the subject at the desired locations. In this manner, each device 100 can remain at the same location and monitor the conditions over time. In particular embodiments, support 102 and sensors 170 may cover and monitor a relatively large area of the patient (e.g. approximately 15 centimeters by 15 centimeters square). Such a configuration can allow a single device 100 to monitor a region of the patient in which pressure ulcers may form without having to remove and re-apply device 100 to test nearby areas. Accordingly, device 100 can remain fixed in a single location at a region of interest and monitor the region on an extended basis. This can allow changes in historical data to be accurately monitored and compared, resulting in improved prediction of pressure ulcers formation.

Particular embodiments relate to methods, devices and systems for visualization of blood flow and oxygenation in any living tissue. Certain embodiments of the device described here use near infrared (NIR) radiation at a plurality of points through a probe in contact with the skin to produce a three-dimensional map of blood flow and oxygenation. A map of the blood flow and oxygenation is created using the detected absorption of the NIR radiation. The methods, devices and systems described herein can detect both the existence and location of arterial occlusions, venous occlusions and other alterations of normal perfusion in a noninvasive fashion. Specifically, the NIRS device may be used for detection of early stage pressure ulcers. Further, the images forming the map can be produced at real-time intervals, such as every second or less.

The NRS device can be placed in contact with the skin of the subject. Specifically, the NIRS device can be encased in an outer flexible material that provides a protective shell for the NIRS device. The NIRS device delivers the NIR radiation (i.e., radiation in the near infrared optical spectrum, 650-1000 nm) up to several centimeters beneath the skin. NIR radiation emitters may emit radiation at multiple light wavelengths. A portion of the NIR radiation is then back-scattered back toward the surface where it is detected by a plurality of radiation detectors, such as photodetectors. This back-scattered radiation provides information about the absorbance within a specific area of the tissue and can be used to produce a color-coded map of the perfusion of the targeted tissue. The color-coded volumetric map, which can be a perfusion map or an oxygenation map or an optical absorption map, is generated using the back-scattered radiation as an indication of the optical properties (such as the optical absorption) at one or multiple wavelengths in each portion of the tissue. The radiation wavelengths are absorbed differently by oxygenated and deoxygenated hemoglobin. The absorption intensity and location provide a pattern based on the oxygenation state of the hemoglobin, which can be incorporated into a three dimensional (3D) map to visualize the oxygenation and deoxygenation of hemoglobin in the tissue. The embodiments disclosed herein are more clearly described with reference to the figures below.

Figure 3:
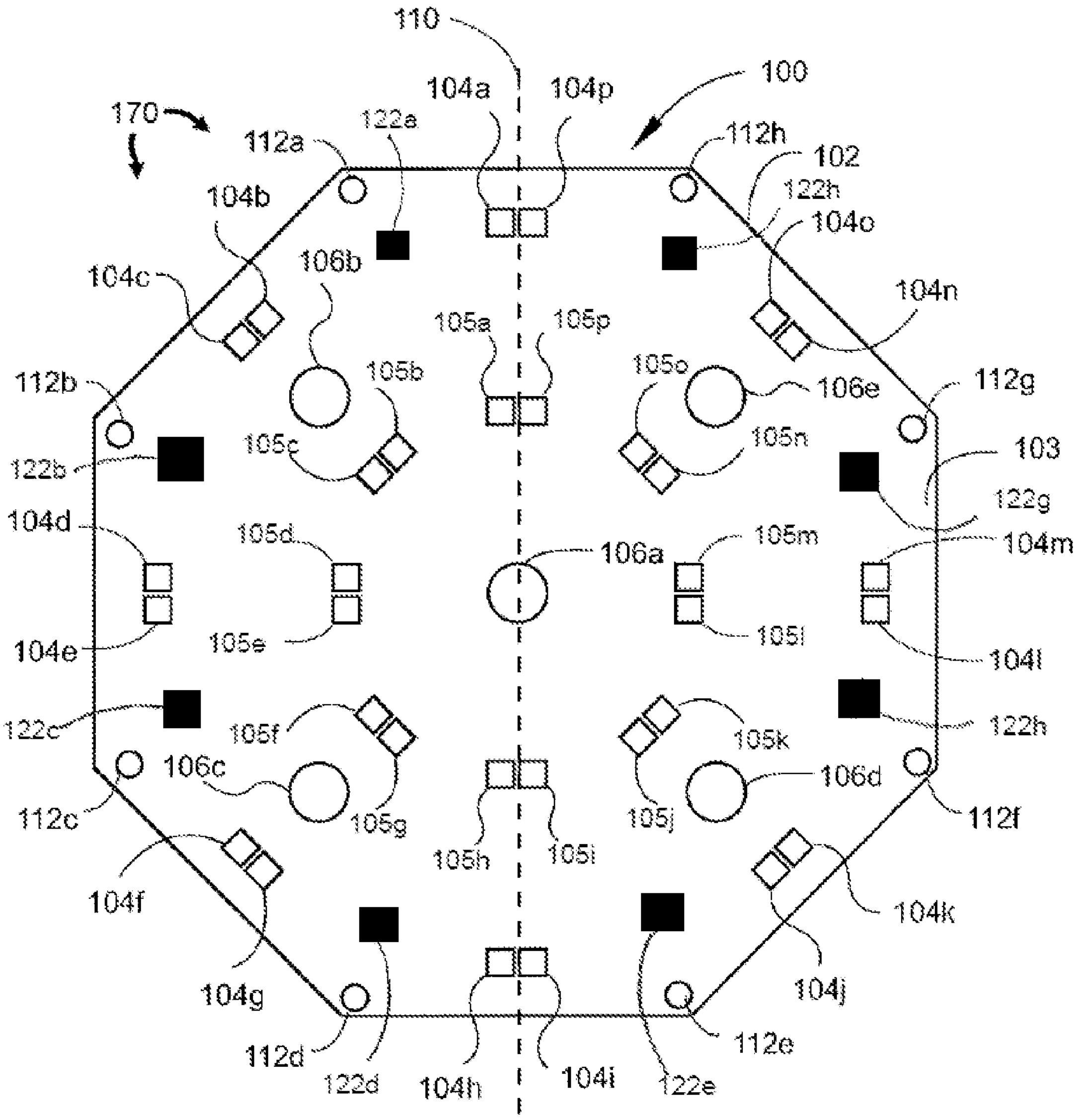
FIG. 3 depicts a view of a device according to an embodiment disclosed herein.

FIG. 3 depicts a top view of a device 100 according to an embodiment. The device 100 includes a support 102 which supports a plurality of additional components of the device 100. The support 102 can be made of a material used in electronic devices, such as phenolic paper, woven fiberglass cloth impregnated with epoxy resin, an insulated metal substrate, and a flexible substrate such as a polyimide foil or polyimide-fluoropolymer composite foil. In one embodiment, the support 102 is a printed circuit board. In certain exemplary embodiments, support 102 is flexible to allow device 100 to accommodate surfaces that are not flat. The support 102 may be of a shape and size to accommodate the area being probed and the needs of the user or the subject. The support 102 shown in FIG. 3 is an octagonal shape, while the support 102 shown in FIG. 1 is a square shape. However, the support 102 can be any shape, including a circle, a square, a triangle, combinations thereof or permutations thereof. The support has a first surface 103 and a second surface (not shown) opposite the first surface. The first surface 103, though depicted as flat, may be flat, curved, wavy or other shapes as needed or desired by the user or the subject.

The support 102 can have a plurality of radiation sources 104*a*-104*p*, 105*a*-105*p*. The radiation sources 104*a*-104*p*, 105*a*-105*p* can be any available source of radiation, such as a light emitting diode (LED), a laser source or other radiation sources. Further, the radiation sources 104*a*-104*p*, 105*a*-105*p* can be light delivery devices in connection with a radiation source, such as a fiberoptic wire in connection with a radiation source listed above. The radiation sources 104*a*-104*p*, 105*a*-105*p* can be discrete components which are positioned on the support 102 or the radiation sources 104*a*-104*p*, 105*a*-105*p* can be integrated into the support 102. In this embodiment, the radiation sources 104*a*-104*p*, 105*a*-105*p* are integrated into the support 102. The radiation sources 104*a*-104*p*, 105*a*-105*p* can be positioned anywhere on the surface of the support. Here, the radiation sources 104*a*-104*p* form a first circle with a center at the center of the support 102 and radiation sources 105*a*-105*p* form a second circle which is concentric with the first circle.

The plurality of radiation sources 104*a*-104*p*, 105*a*-105*p* can be separated into a set, shown here as sixteen (16) groups of two. For example, radiation source 104*b* and radiation source 104*c* are part of a set. However, larger sets of the plurality of radiation sources 104*a*-104*p*, 105*a*-105*p* are possible. For clarity of discussion, the radiation sources 104*b*, 104*d*, 104*f*, 104*h*, 104*j*, 104*l*, 104*n*, 104*p*, 105*b*, 105*d*, 105*f*, 105*h*, 105*j*, 105*l*, 105*n* and 105*p* can also be referred to as the first radiation sources of the set and the radiation sources 104*a*, 104*c*, 104*e*, 104*g*, 104*i*, 104*k*, 104*m*, 104*o*, 105*a*, 105*c*, 105*e*, 105*g*, 105*i*, 105*k*, 105*m* and 105*o* can also be referred to as the second radiation sources of the set. The first radiation sources of each set can be positioned in close proximity or adjacent to the second radiation sources of the set. Further, the first radiation sources and the second radiation sources of each set can be equidistant from one or more of the detectors 106*a*-106*e*. For example, the radiation source 104*d* and the radiation source 104*e* are equidistant from the detector 106*a*. This positioning will allow two separate wavelengths or ranges of wavelengths to be delivered over largely the same area such that the absorption patterns can be determined and mapped. In certain embodiments, an individual radiation source may produce multiple wavelengths that can be detected by multiple detectors. In particular embodiments, an individual radiation source may produce a single wavelength that can be detected by an individual detector.

The radiation sources 104*a*-104*p*, 105*a*-105*p* can produce radiation at wavelengths from about 650 nm to about 1000 nm. In certain embodiments, at least one radiation source of each of the sets of radiation sources produces a range of radiation wavelengths. The range of radiation wavelengths has at least a portion of the wavelengths between about 650 and about 1000 nm, such as between about 800 nm and about 950 nm. In one embodiment, at least one of the radiation sources of the set of radiation sources produces a range of radiation wavelengths including a wavelength of 880 nm. Shown here, the radiation sources 104*b*, 104*d*, 104*f*, 104*h*, 104*j*, 104*l*, 104*n*, 104*p*, 105*b*, 105*d*, 105*f*, 105*h*, 105*j*, 105*l*, 105*n* and 105*p* (the first radiation sources of the set) produce radiation between about 650 nm and about 1000 nm. Further, in certain embodiments, at least one of the plurality of radiation sources 104 produces a range of radiation wavelengths. The range of radiation wavelengths has at least a portion of the wavelengths between about 650 and about 1000 nm, such as between about 650 and about 800 nm. In one embodiment, at least one of the radiation sources of the set of radiation sources produces a range of radiation wavelengths including a wavelength of about 660 nm. The radiation sources 104*a*, 104*c*, 104*e*, 104*g*, 104*i*, 104*k*, 104*m*, 104*o*, 105*a*, 105*c*, 105*e*, 105*g*, 105*i*, 105*k*, 105*m* and 105*o* (the second radiation sources of the set) produce radiation from about 650 and about 1000 nm. In this embodiment, the first radiation sources of each set produce at least one wavelength which is not produced by the second radiation sources of the respective set. In one example, the radiation source 104*b* produces at least one radiation wavelength which is different from the radiation source 104*c*.

The support 102 further includes a plurality of sensors 170 that are configured to detect conditions that can indicate potential formation of a pressure ulcer. In the embodiment shown, sensors 170 include one or more detectors 106*a*-106*e* configured to detect optical properties, sensors 122*a*-122*h* configured to detect changes in temperature and/or humidity. The detectors 106*a*-106*e* can be any device which detects one or more wavelengths of radiation. The detectors 106*a*-106*e* may be photodetectors, such as a photoconductor, a junction photodetector, avalanche photodiodes, other types of detectors which can directly detect radiation, indirectly detect radiation or combinations thereof. The detectors 106*a*-106*e* can be discrete components which are positioned on the support 102 or the detectors 106*a*-106*e* can be integrated into the support 102.

The support 102 can further include one or more sensors 122*a*-122*h*. The one or more sensors 122*a*-122*h* may be temperature sensors that detect temperature or variations thereof. The temperature sensors may be two identical diodes with temperature-sensitive voltage that can monitor changes in thermal dispersion. Other types of temperature sensors may be thermocouples, resistance temperature detectors, or a thermally sensitive resistor. The sensor is connected through the support 102 to a connection such as a wire within the integrated circuit. In another implementation, the sensors 122*a*-122*h* may be humidity sensors that detect moisture or the amount of fluid vapor. In another implementation, the sensors 122*a*-122*h* may be alternating temperature sensors and humidity sensors. For example, sensors 122*a*, 122*c*, 122*e*, and 122*g* may be temperature sensors while sensors 122*b*, 122*d*, 122*f*, and 122*h* are humidity sensors.

Figure 4:
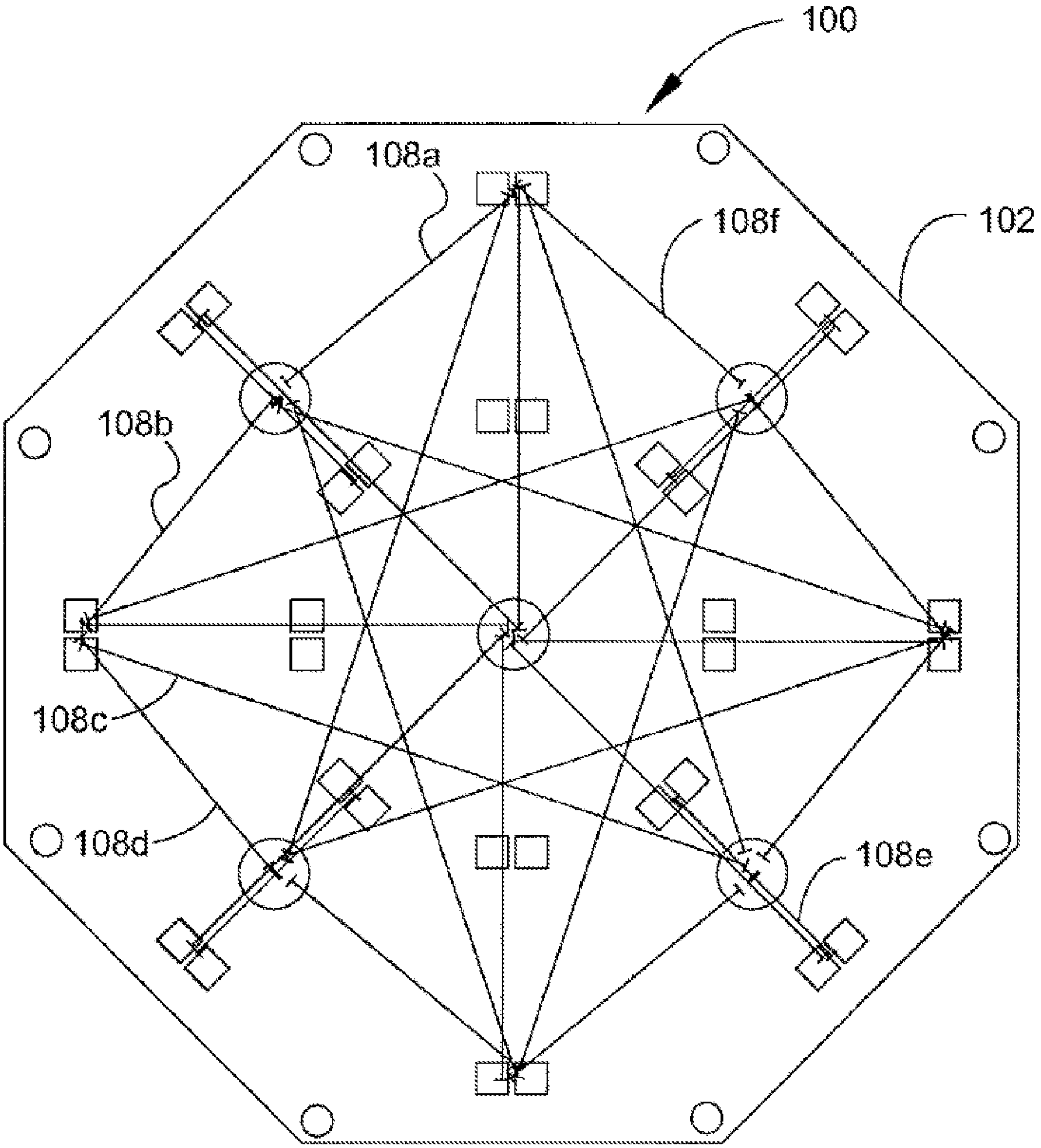
FIG. 4 depicts the device with the plurality of interdistances according to one embodiment disclosed herein.

FIG. 4 depicts the device 100 with the plurality of interdistances according to one embodiment disclosed herein. The interdistance in the space between one of the plurality of radiation sources 104*a*-104*p*, 105*a*-105*p* and one of the plurality of detectors 106*a*-106*e*. As the radiation delivered from each of the radiation sources 104*a*-104*p*, 105*a*-105*p* will diffuse in the tissue in all directions, each of the detectors 106*a*-106*e* will receive some radiation from each of the radiation sources 104*a*-104*p*, 105*a*-105*p*. Therefore, the positioning of the plurality of detectors 106*a*-106*e* and the plurality of radiation sources 104*a*-104*p*,105*a*-105*p* creates a web of interdistances, exemplified here as interdistances 108*a*-108*f*. To maintain clarity, not all interdistances are shown in FIG. 4. In certain embodiments, device 100 may comprise opaque elements between certain radiation sources and detectors to direct light between particular radiation sources and detectors as desired.

Figure 5:
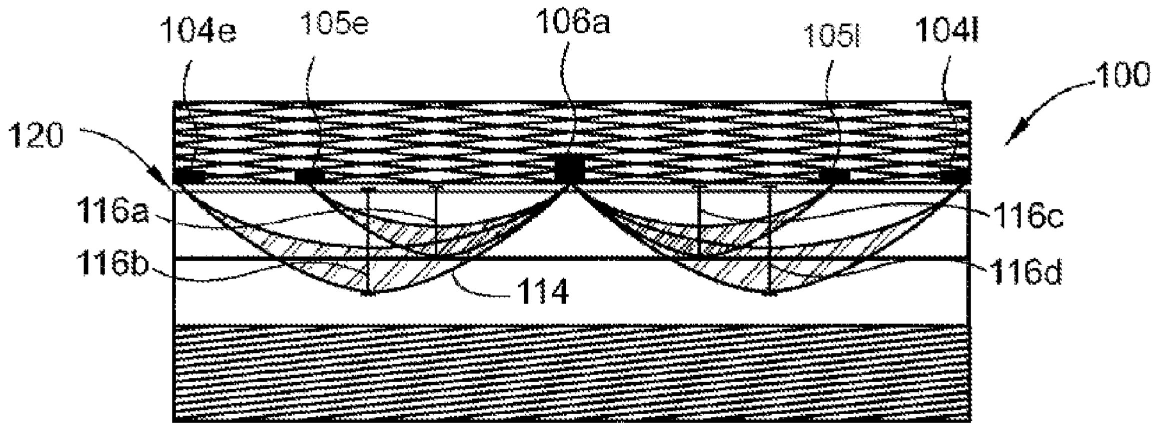
FIG. 5 depicts a side view of the device positioned in connection with a tissue according to an embodiment disclosed herein.

In FIG. 5, the device 100 can be positioned in proximity to a tissue 120. The tissue 120 can be a human tissue, such as on areas that occur over a bony prominence, including for example, an elbow, spine, hip, heel, knee or ankle. In this side view, only detector 106*a* and radiation sources 104*e*, 105*e*, 105*l*, and 104*l* are visible. The detector 106*a* and radiation sources 104*e*, 105*e*, 105*l*, and 104*l* are positioned on the support 102 with a specific interdistance between them. It is believed that the main determinant of the detection depth 116, when composition of the tissue 120 is not considered, is the interdistances between the radiation source and the detector, such as the interdistance between the radiation sources 104*e*, 105*e*, 105*l*, and 104*l* and the detector 106*a*. Radiation that happens to travel close to the surface of the tissue 120 is very likely to be lost out of the tissue 120 before reaching the detector. Thus, interdistance between the radiation source and the detector will not detect most of the radiation which travels close to the surface except in the portion of the tissue 120 directly under the radiation sources 104*e*, 105*e*, 105*l*, and 104*l* and the detector 106*a*. On the other hand, radiation which is not sufficiently scattered, radiation which is scattered in other directions, or radiation which is absorbed by the tissue 120 is not returned to the detector 106*a*. The remaining radiation, excluding the lost radiation between the radiation source 104 and the detector 106 and the distant radiation which does not return to the detector 106, create a mean radiation path 114 in an arcuate shape shown in FIG. 5. By modulating the interdistance between the radiation source 104 and the detector 106, the average detection depth 116 can also be modulated.

Radiation between about 650 nm and about 1000 nm can be used to identify the position and quantity of hemoglobin in the tissue 120. Hemoglobin has a wide absorbance range, for both the HHb and $HbO_2$ states, in the range of about 650 nm to about 1000 nm. The isosbestic point between HHb and $HbO_2$ is about 808 nm. The isosbestic point is a specific wavelength at which two chemical species have the same molar absorptivity. Thus, HHb is the primary absorbing component in the range of between about 650 nm to about 808 nm and $HbO_2$ is the primary absorbing component in the range of between about 808 nm and about 1000 nm. At wavelengths below 650 nm, the absorption of hemoglobin is too high which would prevent anything but superficial measurement of the specific subtype. At wavelengths above 1000 nm, the absorption of water is too high which would prevent measurement of absorption of either HHb or $HbO_2$. Using the absorbance ranges described above, the overall quantity of hemoglobin in an area can be determined while differentiating between HHb and $HbO_2$ in the same area.

As described above, the interdistance between one of the radiation sources 104 and one of the detectors 106 can be used to increase or decrease the detection depth 116*a*-116*d*. It is further believed that the detection depth 116*a*-116*d* at the midpoint between one of the detectors 106 and one of the radiation sources 104 is approximately half of the interdistance between the detector 106 and the radiation source 104. The positioning of the radiation sources 104 and the detectors 106 creates a plurality of mean radiation paths 114. The mean radiation paths 114 are the average path for radiation through the tissue 120, which penetrates to various depths and overlaps with other mean radiation paths 114. The information provided by the mean radiation paths 114 and their overlap can be used to create the three-dimensional map of the HHb and the $HbO_2$ as well as to differentiate between the comparative concentrations thereof.

A plurality of vacuum ports 112, shown in FIG. 3, can be formed in the support 102. The vacuum ports 112 can be connected with a vacuum supply (not shown). The vacuum ports 112 may be of various sizes and shapes, such as the eight circular vacuum ports 112 shown here. The vacuum ports 112 may be formed at the edges of the support 102 or at an internal portion of the surface 103. The vacuum ports 112 may be used to apply a vacuum to an underlying surface, such as the surface of the tissue 120, thus creating a more secure connection between the surface 103 and the tissue 120. In further embodiments, the vacuum ports 112 are omitted and the NIRS device is secured to the tissue 120 using other means, such as through the use of adhesives or bandages. In particular embodiments, device 100 may include a casing 130 that incorporates an adhesive to allow device 100 to be coupled to the patient at the area of examination (e.g. a bony protuberance) in which a pressure ulcer may be likely to form. During use of device 100, the distance between the device 100 and the tissue 120 should be minimized to minimize reflection of the radiation from the surface of the tissue 120. A media interface, such as that which forms at the surface of the tissue 120 in the presence of atmospheric gases, can create a partially reflective surface to the NIR radiation. Reflection from an interface surface is a function of the distance from the surface, as radiation diffuses over a distance in atmosphere. Thus, the surface of the tissue 120 reflects a higher proportion of the wavelengths of NIR radiation when the tissue 120 is spaced a greater distance from the radiation sources 104*a*-104*p*, 105*a*-105*p*. By decreasing the distance between the radiation sources 104*a*-104*p*, 105*a*-105*p* and the tissue 120, either with or without the vacuum ports 112, the effect of reflection at the interface is diminished.

Although the device 100 and the related methods and technological advances are depicted in the context of a specific tissue, such as the skin, the scope of the embodiments disclosed herein are not limited to any specific tissue. The scope of the methods or devices disclosed herein can easily be modified to accommodate other forms of in vivo applications. In one embodiment, the device 100 as described herein, can provide real-time, 3-D volumetric mapping technology without invasive procedure. Thus, the device 100 allows a clinician to assess the adequacy of blood perfusion in an immobile patient.

One or more wireless communication methods or protocols can then be incorporated to receive the information transmitted by the device 100. For example, the oxygenation, temperature, or humidity, information could be sent via Bluetooth or other method to a computing device, such as smartphone, a tablet or a laptop. The computing device can then relay the information to a third party, such as the patient, the patient's provider or another clinician.

Figure 6:
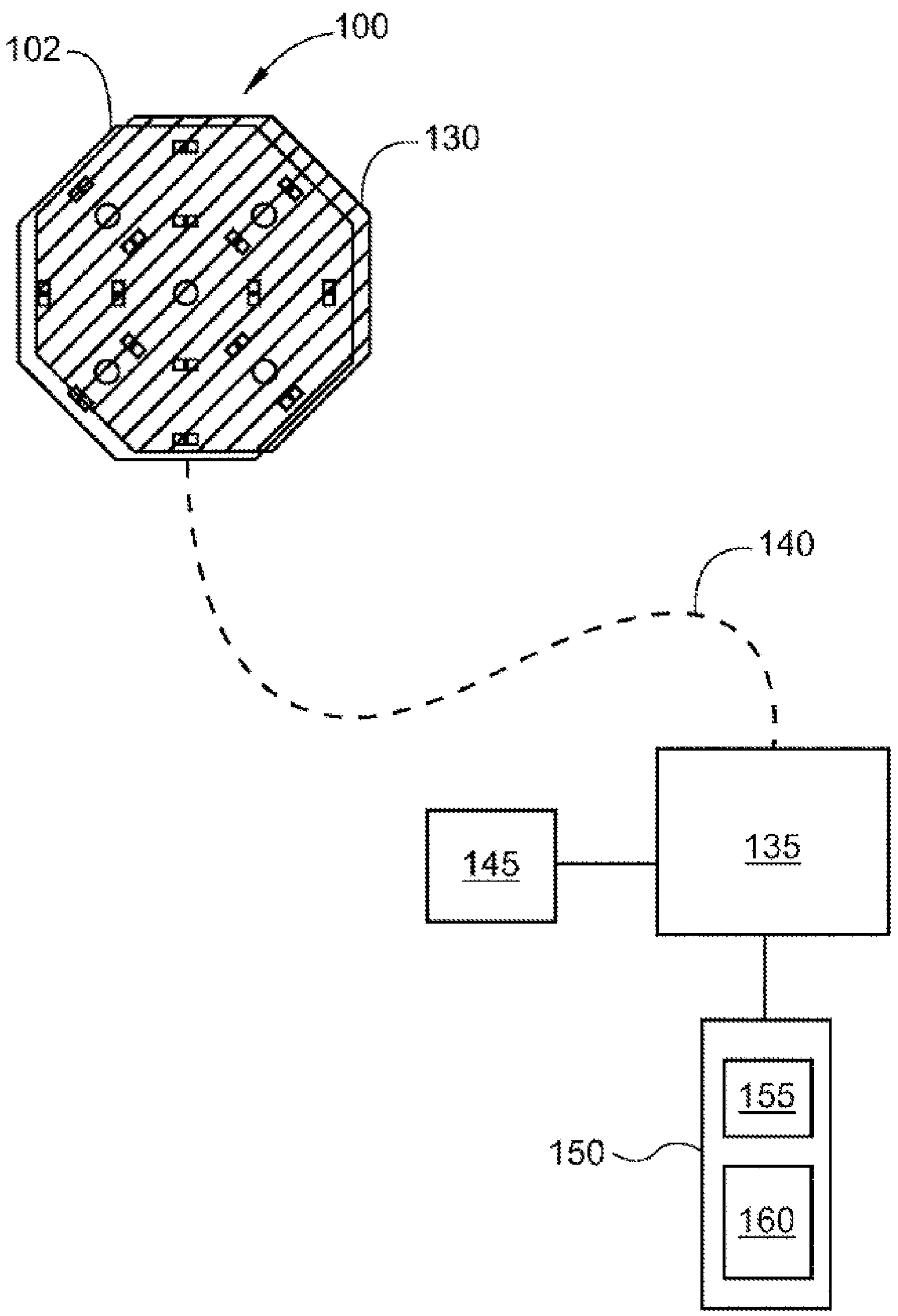
FIG. 6 depicts the device in connection with a data collection unit, according to one embodiment disclosed herein.

FIG. 6 depicts the device 100 in connection with a data collection unit 135 and a control unit 150, according to an embodiment disclosed herein. The device 100 can be connected with the data collection unit 135 through the connection 140. The data collection unit 135 can be a single device or a plurality of devices configured to receive and process the information collected by device 100. In certain embodiments, the signal emitted from a radiation source and/or the signal detected by a radiation detector may be amplified or adjusted to account for different skin pigmentations. The connection 140 between the data collection unit 135 and the device 100 may be either a wired or wireless connection. The connection 140 shown here is a wired connection.

The data collection unit 135 can be in connection with further devices, such as a control unit 150. In some embodiments, the data collection unit 135, the control unit 150, the device 100 or combinations are the same device or device component. The combination of the device 100, the data collection unit 135 and the control unit 150 may be referred to as an imaging device. The control unit 150 can include a processor 155 and memory 160. The control unit 150 can be configured to collect, process or otherwise utilize the received data at the data collection unit 135. The control unit 150 can deliver automated or user-input instructions to the device 100 to perform one or more of the functions described with reference to FIG. 3-5. The control unit 150 can also be a smartphone, an interactive display or other devices. In another embodiment, the data collection unit 135 is a computer including a processor and memory with instructions which, when processed by the computer, causes the computer to perform one or more of the functions described herein. The data collection unit 135 is connected with a power supply 145, which powers the data collection unit 135, the device 100, the control unit 150 or combinations thereof. The data collection unit 135 can also be connected with further devices through a wireless transmitter. In one embodiment, the data collection unit 135 provides information collected by the device 100 to a remote location, e.g. a nursing station down the hall, a doctor's office or a call center. Using the control device 150, the data collection unit 135 or both, an individual (e.g., a doctor or a nurse) can track changes in tissue perfusion in near real time and perform intervening measures such as moving the individual to prevent the further progression of the ulcer.

The processor can be a general use processor, as known in the art. Further, the processor can be designed for the specific functions that are disclosed herein. The processor can be designed or configured to perform one or more operations related to the detection of a near infrared signal or for the determination of oxygenation in a tissue, temperature, and humidity. The operations may be represented as instructions in a machine-readable format that are stored on the memory. The memory can be one or more non-transitory types of computer readable media, such as solid state memories, hard drives, and the like. The instructions may reside completely, or at least partially, within the memory and/or within the processor during execution.

In further embodiments, the device 100 can be coated or within a casing 130. The casing 130 can be an optically clear biocompatible material, such as silicon. The casing 130 can prevent direct contact between the tissue 120 and electronic components without compromising the functionality due to light reflections. The casing may disperse the pressure placed on the device. For example, the encasing may be square, rectangular, circular, elliptical, or any other geometric shape to conform to the various curvatures it is placed on. In one implementation, the encasing is heart shaped. Additionally, the device 100 may be incorporated into other devices, such that a first device incorporates the functionality of the device 100.

Figure 7:
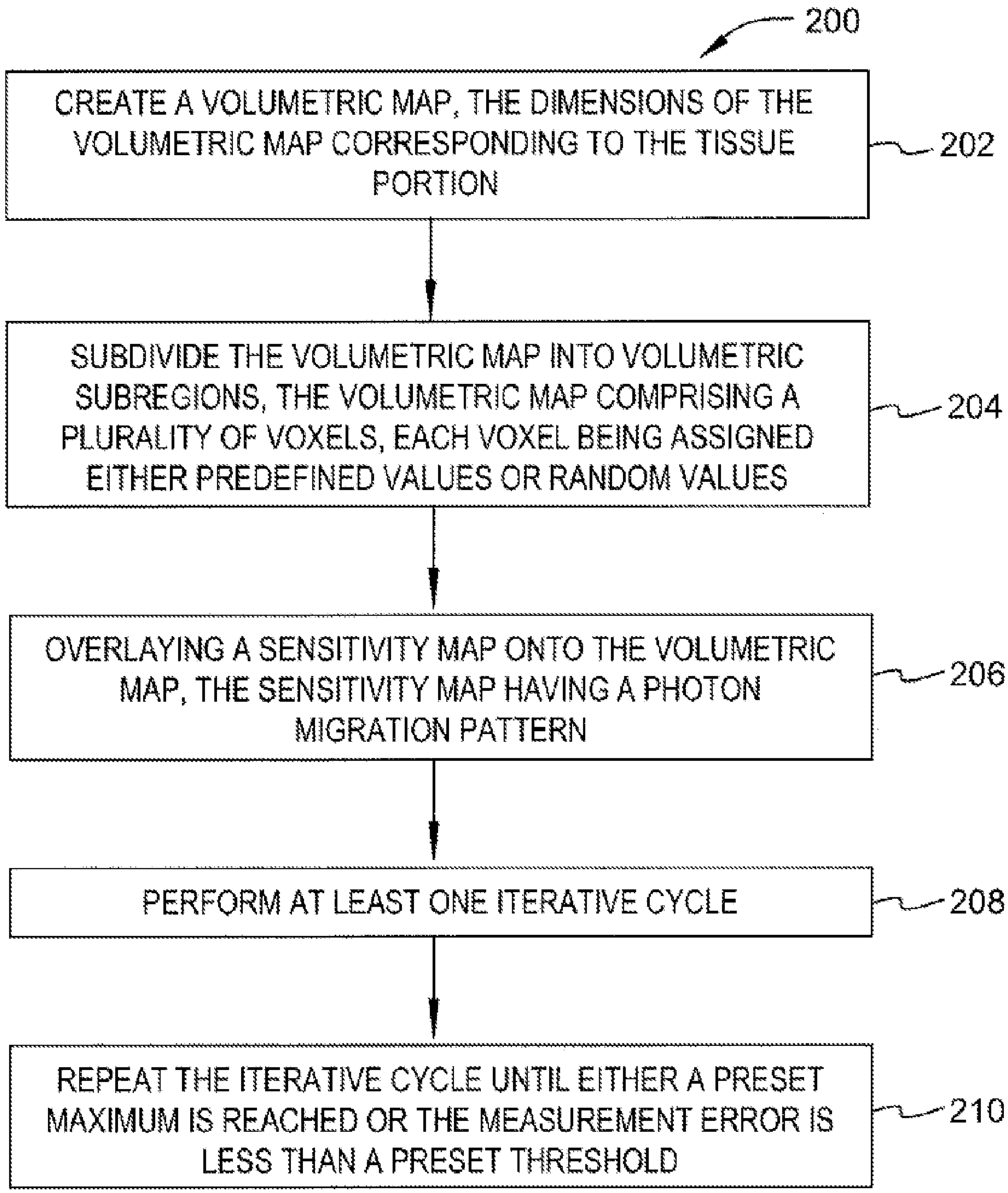
FIG. 7 is a block diagram of machine-readable instructions for processing near infrared spectroscopy information, according to one embodiment.

FIG. 7 is a block diagram of machine-readable instructions 200 for processing near infrared spectroscopy information, according to one embodiment. The memory can be adapted to store a plurality of machine-readable instructions. The machine-readable instructions 200 can, when executed by the processor, cause the imaging device to create a sensitivity map of a tissue portion, the sensitivity map showing a photon migration pattern for the tissue portion, and create a volumetric map. The dimensions of the volumetric map can correspond to the tissue portion in certain embodiments. The instructions 200 can then subdivide the volumetric map into volumetric subregions, the volumetric subregions comprising a plurality of voxels, each voxel being assigned either preassigned values or random values. The instructions 200 can then overlay the photon migration pattern of the sensitivity map onto the volumetric map and perform at least one iterative cycle. The instructions 200 may repeat the iterative cycle until either a preset maximum is reached or the measurement error is less than a present threshold.

In certain embodiments, the machine-readable instructions 200 can, when executed by the processor, cause the device to create a temperature map, wherein the dimensions of the temperature map correspond to a thermal dispersion pattern. The temperature map may be created in addition to the volumetric map in certain embodiments, or in lieu of the volumetric map in other embodiments.

In particular embodiments, the machine-readable instructions 200 can, when executed by the processor, cause the imaging device to create a humidity map, the dimensions of the humidity map corresponding to a fluid vapor amount.

In specific embodiments, the dimensions of the created volumetric map correspond to the tissue portion, as shown in step 202. The volumetric map is the same volume as the tissue portion being examined by the NIRS device. The volumetric map begins with no information incorporated, and the volumetric map consists of a plurality of voxels. The voxels are defined regions of the volumetric map representing the smallest distinguishable detection area in the volumetric map.

Instructions 200 can further include subdividing the volumetric map into volumetric subregions, at 204. In one embodiment, the volumetric map is further divided into volumetric subregions. The volumetric subregions are defined three dimensional regions in the volumetric map. The volumetric subregions can be non-overlapping. Further, the volumetric subregions can share common boundaries, such that 100 percent of the volumetric subregions is equivalent to 100 percent of the volumetric map. Stated another way, the volumetric subregions can be composed of the plurality of voxels. The volumetric subregions can be formed such that the boundary of the volumetric subregion does not subdivide a voxel. The number of sub-regions can be fixed or can be dynamically changed throughout the algorithm. In one embodiment, the volumetric subregions are dynamically changed by the exclusion of a determined sub-region, such that the process focuses on sub-regions which have not yet been determined. In another embodiment, the volumetric subregions are dynamically changed by changing the position of the boundaries of the defined subregions, such that either the shape of the subregions change, the position of the subregions change or the number of subregions change.

Instructions 200 can further include assigning each voxel with either preassigned values or random values. As each voxel corresponds to a portion of the tissue, it also has a volumetric value, such as an oxygenation value, that describes or relates to the detected parameter in the corresponding portion of tissue. As it is not currently feasible to deliver radiation to each voxel individually and detect the related absorbance, information must be extrapolated from the optical measurement and onto the voxels of the volumetric map. The program described herein extrapolates this information by providing an assumed volumetric value for each of the voxels, based on either a predefined number or a random number. Possible volumetric values include optical absorption measurements, corresponding readings of concentration of hemoglobin in various states, such as oxyhemoglobin ($HbO_2$) and deoxyhemoglobin (HbB), or other entries which correlate to an optically measurable tissue data.

Instructions 200 can further include overlaying a sensitivity map onto the volumetric map, the sensitivity map having a photon migration pattern, at 206. It is beneficial to know where the photons migrate within the tissue of interest, given the superficial location of all sources and detectors. Specifically, the photon path between each source and each detector of the probe can be determined and then superposed for all source-detector pairs, so to obtain a volumetric map that describes the density of photons in all locations within the tissue. This is called the sensitivity map. The sensitivity map is intended as the map that indicates which sub-regions of tissue, and which voxels, are more sensitive to the detection of a physiological change. The sensitivity is due to a higher density of photons travelling in those regions. In contrast, physiological changes in regions of the tissue where there is no photon travelling will not be directly measurable by optical absorption (i.e., region of the sensitivity map that has a null sensitivity). The sensitivity map relates to the geometric layout of light sources and detectors and to the anatomical properties of the tissue being investigated.

The reconstruction of a volumetric map of blood perfusion or changes thereof can be described as an inverse problem. An inverse problem is a problem where the effect of a physiological phenomenon is known (e.g., by taking single or multiple measurements at any given point in time, for a single or multiple points in time) and a description of the originating phenomenon (e.g., the quantity of oxyhemoglobin ($HbO_2$) and deoxyhemoglobin (HbB)) is sought as a result. As opposed to the “forward problem” (which is calculating the measurable effect of a known originating phenomenon), the inverse problem is substantially more difficult to solve, mainly because a dense representation of the source (in one example, a perfusion image consisting of thousands of voxels) is attempted starting from sparse measurements of the effect (i.e., few dozens of optical measurements).

One approach to the solution of the inverse problem is an iterative approach. The volumetric map is initially defined, as described above, and it is subsequently adjusted over a certain number of iterations, until the volumetric map is deemed to be sufficiently accurate. The strategy for adjusting the map at any step of the iterative cycle is based on the error between the actual measurements of the effect (optical measurements or concentration measurements) and the measurements calculated by solution of the forward problem using the estimated volumetric map. As described here, the sum of the assumed volumetric values is then transformed using the sensitivity map.

If the error has a downward trend during subsequent map adjustments, then the applied adjustments to the map are going in the right direction and the volumetric map is converging towards a solution of the inverse problem. If the error has an upward trend during subsequent map adjustments, then the applied adjustments are wrong and must be corrected in subsequent iterations. The iterative process ends when the error between the actual and estimated measurement is sufficiently low, indicating that the current estimated volumetric map is in fact originating an effect measurement that is sufficiently close to the actual measurement.

To solve the forward problem, it is necessary to know where the photons migrate within the tissue of interest, given the location of all sources and detectors in the NIRS device. Specifically, the photon migration pattern between each source and each detector of the probe need to be determined. The photon migration pattern can then be superposed for all source-detector pairs, which creates a sensitivity map that describes the density of photons derived from the source in all locations within the tissue portion.

Instructions 200 can further include performing at least one iterative cycle, at 210. The iterative cycle can include determining the measurement array and the calculated array for the volumetric map. The measurement array includes an optical measurement for the areas corresponding to the photon migration pattern in the volumetric map. The calculated array includes a determined measurement of the equivalent migration pattern of the volumetric subregion. The optical measurement is the optical measurement of the radiation delivered from each of the radiation sources to the tissue and received by each of the detectors, as affected by absorbance in the corresponding region of tissue (i.e., the tissue in the photon migration pattern). The determined measurements is the calculated equivalent to the optical measurement, as calculated from the voxels of the volumetric map which correspond to the photon migration pattern and weighted based on the sensitivity map.

The tissue can include a plurality of layers, such as a first layer, a second layer and a third layer. The first layer can be skin layer, the second layer can be an adipose layer and the third layer can be a muscle layer. The first layer, the second layer and the third layer may be composed of one or more individual sub-layers (not shown). Further, though the first layer, the second layer and the third layer are depicted here as discrete layers, the layers may not form a distinguishable boundary. Hemoglobin may be interspersed in the first layer, the second layer and the third layer. The hemoglobin can be found in distinct vessels (e.g., arteries, veins, arterioles, venules, and capillary beds) which are interspersed in the first layer, the second layer and the third layer.

In one embodiment, the measurement is a single measurement for all radiation source/detector combinations. The single measurement can be used throughout all iterative cycles. Each of the measurement array and the calculated array include a number of values related to the total number of radiation source/detector combinations. In one embodiment, there are sixty-four (64) radiation source/detector combinations. Therefore, in this embodiment, there are sixty-four (64) actual optical measurements in the measurement array and 64 determined measurements in the calculated array.

The iterative cycle can further include increasing an assigned value of a test voxel and calculating a perturbed calculated array for the volumetric map, wherein the volumetric map is perturbed at a test voxel within the selected subregion. Using the embodiment described above, a single assigned value is changed for a test voxel. The assigned value can be a perfusion value. The 64 determined measurements for the calculated array are produced from the volumetric map. The 64 determined measurements (i.e., the calculated array) are then compared to the 64 actual optical measurements (i.e., the measurement array) to determine the distance between the values.

Each of the test voxels are selected from the voxels of the volumetric subregions. As stated above, the voxels of the volumetric map are given an assigned value, which can be either arbitrary or predefined. When the test voxel is increased in value, the increase will perturb the value of the measurement corresponding to the volumetric subregion. The perturbed calculated array, which is the sum of the values of the voxels in the volumetric map as transformed by the sensitivity map, can then be calculated for each of the photon migration patterns.

In one embodiment, predefined can mean defined through a previous iterative cycle. The iterative process converges faster when the value assigned to the voxels of the volumetric map at the first iteration is close to the real solution. As such, the algorithm can include the creation of a pre-measurement volumetric map of the tissue. The pre-measurement can have a longer than standard duration (e.g., 10-60 seconds, considering that it starts from a null, or unknown image). The pre-measurement voxel values can then be used to set the initial value of the voxels for future measurements. It is believed that, because the physiological changes occur quite slowly (in the order of tenth of seconds or minutes), that an image calculated at a previous point in time would provide values which approximate the volumetric map at a current point in time. Further, any physiological traits of the tissue portion which affect an oxygenation parameter will be represented to some extent in the pre-measurement volumetric map. As such, by using the individually established values from a pre-measurement for the base value for the voxels in a later iterative cycle, the values will be both more quickly derived and more precise than arbitrary values or preassigned values which are established in another fashion.

The iterative cycle can further include determining the error between each of the optical measurements of the measurement array and the perturbed determined measurement of a perturbed calculated array. The error is determined using the Euclidean distance between the two points P and Q, where P is the measurement array and Q is the calculated array. The Euclidean distance between points P and Q is the distance between the points in a Euclidean space of n-dimensions (n-space). Thus, the distance between the points correlates to the error in the perturbed determined measurements of the perturbed calculated array. In one example, a total of 64 photon migration patterns creates a total of 64 optical measurements for the volumetric map. The 64 optical measurements are the P values, which are compared against the 64 perturbed determined measurements (i.e., the Q values). The distance between these points is the magnitude of the error. In Cartesian coordinates, if $P=(P_1, P_2, \ldots, P_n)$ and $Q=(Q_1, Q_2, \ldots, Q_n)$ are two points in Euclidean n-space, then the distance (d) from P to Q, or from Q to P is given by:

$$d(p, q) = d(q, p) = \sqrt{(q_1 - p_1)^2 + (q_2 - p_2)^2 + \ldots + (q_n - p_n)^2} = \sqrt{\sum_{i=1}^{n} (q_i - p_i)^2}.$$

If the perturbation causes the measurement error to go down, then a volumetric Gaussian kernel of sigma value S (similar to the radius of a sphere) is centered on the perturbed voxel and is permanently increased in perfusion proportionally to the magnitude of the error decrease multiplied by a proportional factor A. If the perturbation causes the measurement error to go up, then the perfusion map is updated by decreasing the perfusion locally in a volumetric Gaussian kernel of sigma value S and centered on the perturbed voxel and is permanently decreased in perfusion proportionally to the magnitude of the error increase multiplied by a proportional factor A. The machine-readable instructions 200 can be executed sequentially or in a predetermined order.

The sigma value S is an assigned value which corresponds to the radius of the Gaussian kernel from a starting point of the center of the test voxel. The value S is not necessarily a static value and can change throughout the iterations. The proportional factor A is an intensity value which determines the proportion of change in voxel value within the Gaussian kernel. The factor A is not necessarily a static value and can change throughout the iterations. If value of distance (d) is increased from the baseline measurement (e.g., the distance between P and Q based on the measured value and the original assigned value), then the perturbed voxel and surrounding region are adjusted down by an order of magnitude using the above described Gaussian kernel transformation. If this value is decreased from the baseline measurement, then the perturbed voxel and surrounding region are adjusted up by an order of magnitude using the above described Gaussian kernel transformation.

The instructions 200 can further include repeating the iterative cycle until either a preset maximum number of iterations is reached or the measurement error is less than a preset threshold, at 210. The preset maximum is a maximum number of events until number the iterative cycles are deemed to be sufficient. The preset maximum can be a number of iterative cycles, an amount of time or other maximum attributes as defined by the user. The preset threshold is a boundary set for the measurement error. The preset threshold can be less than 5 percent error, such as less than 1 percent error.

In operation of certain embodiments, the radiation sources of the system produce a NIR radiation which is directed toward the tissue. The NIR radiation penetrates the first layer, the second layer and the third layer. The tissue causes a distortion in the directionality of the NIR radiation, based on the scattering property of the tissue. The scattering property of the tissue, including the scattering coefficient, relates to the composition of the tissue. Table values can be used to determine the scattering coefficient of specific tissue types which may form the layers of the tissue. Further, the scattering coefficient can be determined using other measuring techniques, including optical techniques. If the scattering coefficient is low, the radiation would simply travel through and not reflect, refract or otherwise change direction. Without back-scattering, the NIR radiation would not be received by the detector. The layers of the tissue, such as skin and adipose tissue, are high scatterers of the NIR radiation. As such, part of the NIR radiation is redirected back toward the detector. The absorption coefficient is a measured parameter and is determined by the absorption of the NIR radiation by the tissue as a function of the original radiation intensity.

The back-scattered radiation is the NIR radiation first sent, as reduced by passing through the tissue and by specific wavelengths at the hemoglobin. The back-scattered radiation will be affected by a variety of factors before being received by the detector, such as the radiation angle of incidence, tissue type, depth of travel, absorption and the like. The back-scattered radiation will include the wavelengths provided by the radiation source without a portion of the NIR radiation which is absorbed by the hemoglobin. The portion of the NIR radiation that is absorbed by the hemoglobin and other factors (such as water and less plentiful chromophores) in relation to the total input of the NIR radiation is used to create the map. The pathway of the NIR radiation and the back-scattered radiation is not necessarily linear. The NIR radiation and the back-scattered radiation will be back-scattered by numerous components of the tissue.

The NIRS system will be configured to calculate the oxygenation value of each volume element of the matrix (also known as a voxel) as a weighted sum of the measured oxygenation of all mean radiation path volumes that each voxel belongs to. The NIRS system will also be configured to process the oxygenation matrix to generate and display topographic and fMRI-like tomographic views of the blood perfusion within the tissue. The absorbance at each of the mean radiation paths of each combination of radiation sources and detectors are compared to one another. The absorbance for each of the mean radiation paths is determined in relation to the wavelength absorbed. The absorbance from the overlapping mean radiation paths or derived information from the absorbance is then plotted on a coordinate plane to produce a map.

By determining the area of overlap for the known mean radiation path, a portion of the absorbance for each of the mean radiation paths can be attributed to that portion based on the area of the overlap with consideration of the x, y and z planes. The overlap of the areas of overlap as mapped on the x, y and z planes provides the three dimensional information regarding oxygenation in the tissue. Increased overlap of areas of overlap gives more accurate boundaries for HHb and $HbO_2$, as the absorbances will be different between mean radiation paths. For example, comparison of the overlap absorbance of areas of overlap for mean radiation paths with a wavelength range including 660 nm with the overlap absorbance of overlapping mean radiation paths with a wavelength range including 660 nm will provide information on the quantity of HHb in both of the areas of overlap for the mean radiation paths.

Cross comparison between separate wavelengths, such as a comparison of the overlap absorbance of areas of overlap for mean radiation paths with a wavelength range including 660 nm and the overlap absorbance of areas of overlap for mean radiation paths with a wavelength range including 880 nm, will produce data regarding the positioning of hemoglobin in the two regions as well as the comparative oxygenation in the region of overlap. The comparative absorption data is then mapped in a 3D matrix, such as through the use of the MATLAB software, available from Mathworks, Inc. located in Natick, MA. A MATLAB algorithm can be used to generate a 3D matrix. The 3D matrix can include all combination of radiation sources, temperature sensors, humidity sensors, and detectors of the NIRS device, or a portion thereof.

Figure 8:
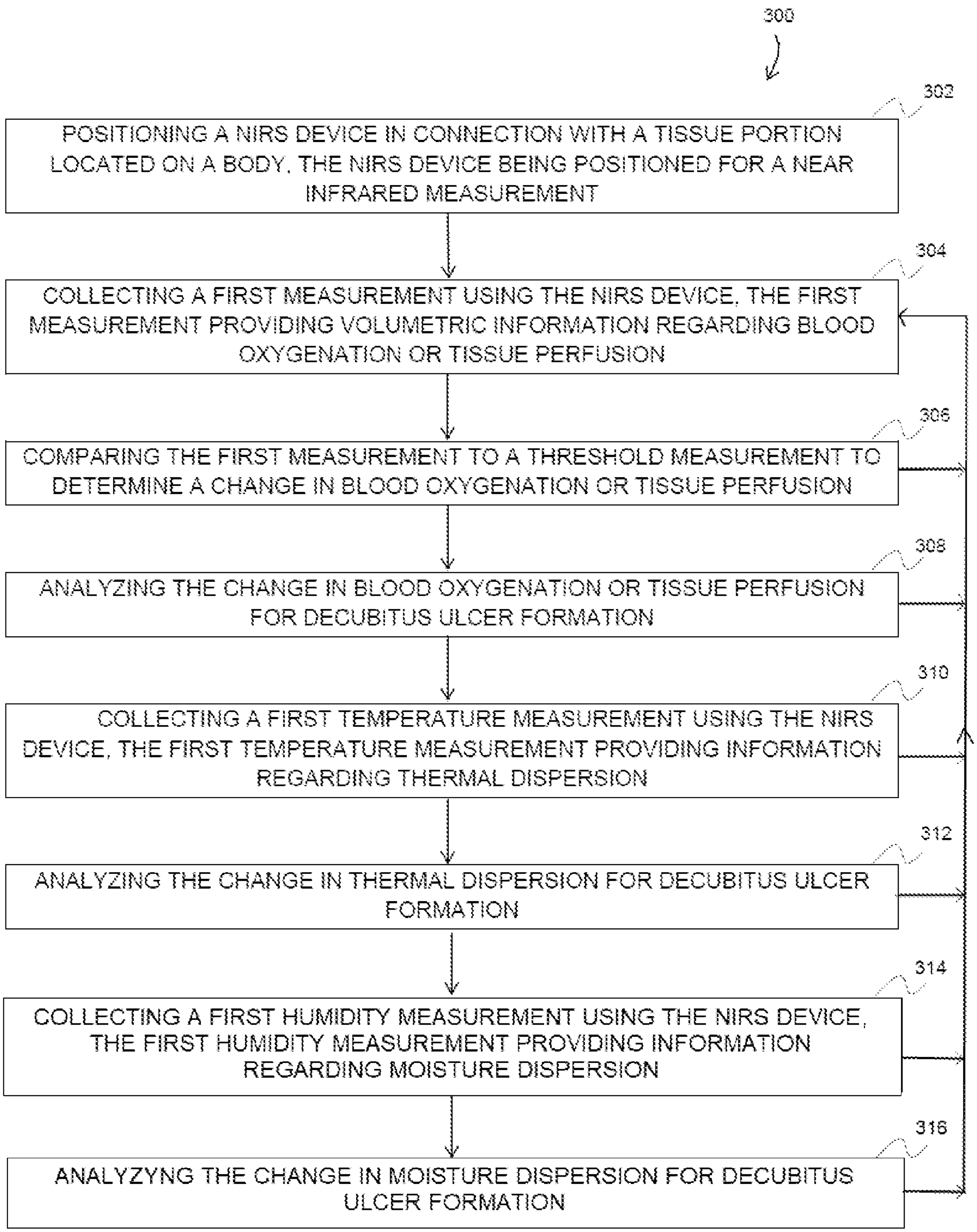
FIG. 8 depicts a flow diagram of a method of ulcer detection, according to one embodiment.

FIG. 8 depicts a block diagram of a method 300 comprising steps 302-316 for determining perfusion of a tissue according to an embodiment disclosed herein. The method 300 can include tissue, as in element 302. In certain embodiments, the tissue comprises both oxygenated and deoxygenated hemoglobin. Generally, the tissue is from a patient and is positioned in proximity to a bony prominence that are at high risk for pressure ulcers. In one implementation, the tissue is on the posterior side of the patient. The near infrared spectroscopy (NIRS) device is positioned in connection with a tissue portion located on a body. The NIRS device being positioned for a near infrared measurement.

A first radiation source and a second radiation source are positioned in proximity to the tissue, as in element 304. The first radiation source and the second radiation source can be a radiation source as described with reference to FIG. 3. The first radiation source and the second radiation source are directed toward the tissue to deliver NIR radiation to the tissue. The first radiation source and the second radiation source can have a fixed distance from one another. Further, the first radiation source and the second radiation source can be positioned at a fixed distance to one or more detectors. Though described here as two radiation sources, a plurality of radiation sources may be used.

Once the radiation source is positioned, a first radiation can be delivered to the tissue. In particular embodiments, the first radiation can have a wavelength range of between about 650 nm and about 1000 nm. The tissue is at least partially transparent to the first radiation allowing the first radiation to travel a distance in the tissue. As the tissue is not homogenous, some components of the tissue, such as hemoglobin, will either absorb the first radiation, transmit the first radiation or reflect the first radiation based on the wavelength of the first radiation received. Radiation which is not absorbed is transmitted through the tissue creating a first transmitted radiation (also referred to as back-scattered radiation).

At least part of the first transmitted radiation is detected at a first detector. The first detector is positioned a first distance from the radiation source. The path that the radiation travels from the radiation source to the detector is the mean radiation path. The first distance determines the length of the mean radiation path from the radiation source to the detector as well as the depth of the detection. The hemoglobin, both HHb and $HbO_2$, within the mean radiation path will provide information in the form of absorption of the first radiation in the mean radiation path. The first transmitted radiation received at the detector can then be used in conjunction with other information to determine the contents of the mean radiation path.

The wavelength used, as described above, is important to the determination of the contents of the mean radiation path. The first NIRS measurement is collected using the NIRS device. The first NIRS measurement provides volumetric information regarding blood oxygenation or tissue perfusion. The first detector detects the intensity of the first transmitted radiation of the wavelength produced by the radiation source. The intensity of the first transmitted radiation delivered to the detector will be affected by the overall amount of the first radiation within the mean radiation path and the amount of the first radiation which is absorbed by components which are spatially within the mean radiation path. The amount of the first radiation within the mean radiation path is a function of the absorption coefficient and the scattering coefficient of each layer of the tissue, which is empirically determined either prior to or during the measurement. The absorption is dependent on the wavelength used and the absorbing components in the tissue, which in this case are HHb and $HbO_2$. Both subtypes absorb radiation of wavelengths between about 650 nm and about 1000 nm to some degree. However, since 808 nm is the isosbestic point for HHb and $HbO_2$, the absorption by HHb is higher at wavelengths below 808 nm and $HbO_2$ is higher at wavelengths above 808 nm.

Once the first transmitted radiation is detected, a second radiation can be delivered from a second radiation source to the tissue. The second radiation source can have a wavelength between about 650 nm and about 1000 nm. The second radiation can be a single wavelength or a combination of wavelengths. Further, the second radiation can include one or more of the same wavelengths as the wavelengths of the first radiation. The tissue can absorb a portion of the second radiation creating a second transmitted radiation.

The second transmitted radiation is then detected at the detector positioned a second distance from the second radiation source. The path travelled by the second transmitted radiation through the tissue creates a second mean radiation path. The second distance may be the same as the first distance, such as when the first radiation source and the second radiation source are positioned in concentric circles which are at a specific radius from a centrally located detector.

The available radiation sources, such as the first radiation source and the second radiation source, are multiplexed, assuring that any one detector is only receiving radiation from one radiation source at any given time. As used herein, "multiplexed" refers to the delivery of the radiation from the source to the tissue and ultimately to each of the detectors, such that each of the detectors only receive radiation from one source at any given time. In one embodiment, multiplexing is done by timing the radiation delivery of each radiation source, such that no more than one radiation source is delivering radiation at any given time. Here, the first radiation is emitted from the first radiation source and a portion of the first radiation is received by the detector as the first transmitted radiation. Once the first transmitted radiation is received, the second radiation source emits the second radiation, a portion of which is received by the same detector. Thus when using time multiplexing, only one optical source is active at a time. Hence, the light detected by one or more photodetectors can be associated with the only radiation source active in that moment. Multiplexing the radiation sources both allows the control unit to differentiate between the sources of the radiation and allows for a larger number of mean radiation paths.

Though the multiplexing above is described with relation to time, the separation of optical signals emitted by distinct emitters (i.e., in distinct locations and/or distinct wavelengths) towards one (or more) photodetectors can be achieved with several techniques, such as time multiplexing (described above), frequency multiplexing, and code multiplexing.

With frequency multiplexing, the radiation sources are separated based on the frequency of the radiation produced by the radiation sources, such that the radiation sources can emit radiation simultaneously. To separate the signals received by the detector, the active radiation sources are modulated at a different frequency. In one example, three radiation sources, R1, R2 and R3, deliver radiation at 660 nm to a tissue. The wavelengths used herein are exemplary. Any wavelength or range of wavelengths for the determination of HbO2 and HHb as described here may be used. As described here, R1 produces the 660 nm radiation at a first frequency, F1; R2 produces the 660 nm radiation at a second frequency, F2; and R3 produces the 660 nm radiation at a third frequency, F3. As R1, R2 and R3 are delivering their radiation simultaneously, the radiation will be received at the detector as a single composite signal. The single composite signal yielded by the detector can then be demodulated at frequencies F1, F2 and F3 to reconstruct the three radiation signals which would have been obtained if the three radiation sources were emitted separately.

With code multiplexing, the radiation sources are separated based on information encoded into the radiation from the radiation sources, such that the radiation sources can emit radiation simultaneously. To separate the signals received by the detector, the active radiation sources are encoded with different codes. In one example, three radiation sources, R1, R2 and R3, deliver radiation at 880 nm to a tissue. As described here, R1 produces the 880 nm radiation with a first code, C1, embedded therein; R2 produces the 880 nm radiation with a second code, C2, embedded therein; and R3 produces the 880 nm radiation with a third code, C3, embedded therein. As R1, R2 and R3 are delivering their radiation simultaneously, the radiation will be received at the detector as a single composite signal. The single composite signal yielded by the photodetector can then be decoded using C1, C2 and C3 to reconstruct the three original signals which would have been obtained if the three sources were emitting in a time-multiplexed fashion.

Once the second transmitted radiation has been detected, an overlap absorbance between the first mean radiation path and the second mean radiation path can be determined and analyzed for pressure ulcer formation, as in element 308. The first mean radiation path is calculated to have a specific three dimensional shape, based on the tissue, the interdistance between the first radiation source and detector, scattering coefficient and other factors. The second mean radiation path is calculated to have a specific three dimensional shape, based on the tissue, the interdistance between the second radiation source and detector, scattering coefficient and other factors. The three dimensional shapes of the mean radiation paths are associated with the detected absorbance for each of the first transmitted radiation (the first mean radiation path) and the second transmitted radiation (the second mean radiation path), respectively. Assuming that there is overlap between the mean radiation path for the first transmitted radiation and the second transmitted radiation, the overlap absorbance is then determined. The overlap absorbance is a weighted absorbance of each of the first mean radiation path and the second mean radiation path based on the respective intensities and the size of the overlap. The first absorbance, the second absorbance and the overlap absorbance in coordinate space act as in conjunction to provide position and intensity of the oxygenation state of the hemoglobin in the tissue. The plurality of temperature detectors can concurrently create a temperature map corresponding to a thermal dispersion pattern. The temperature detectors can simultaneously provide the intensity of thermal output of the tissue. The plurality of humidity detectors can concurrently create a humidity map corresponding to the amount of fluid vapor on the tissue. The temperature detectors and humidity detectors can continuously read the output of the tissue to determine a plurality of points. Each reading creates a point. The plurality of points can be used to determine the temperature map and/or humidity map.

The sequence of delivery of the first radiation, the detection of the first transmitted radiation, the delivery of the second radiation, the detection of the second transmitted radiation, the detection of a first temperature, the detection of first humidity, and the determining of the overlap absorbance are then repeated to create a plurality of overlap absorbances, as in operation 310. A more complete view of the oxygenation can be derived by increasing the number of sources and detectors as well as widening the space over which the detection occurs. Overlapping mean radiation paths using wavelengths both above and below the isosbestic point, allow for positioning and separation of HHb and $HbO_2$.

Finally, the plurality of overlap absorbances is then mapped on a coordinate plane, as in element 312. The position of the overlap absorbance is known in comparison to the device. As such, the overlap absorbances are then plotted on an x, y, and z axis with relation to the position of the device, where the position of the device is an arbitrary position in the coordinate plane. The position of the device can be mapped as well. The higher the number of overlapping mean radiation paths and the higher the number of overlapping areas of overlap at various wavelengths, the better the resolution of the image produced. Further, the longer the interdistance between the radiation sources and the detectors, the deeper the mean radiation path. The method above can be performed in a continuous fashion, such that the map of the tissue is updated in near real-time.

EXAMPLES

In this pilot study, we evaluated the ability of diffuse optical imaging (DOI), i.e. an imaging technique based on near infrared spectroscopy (NIRS), to assess hemodynamic changes resulting from prolonged pressure on the sacral tissues of healthy individuals. Briefly, NIRS measures the optical absorption of two dominant chromophores in human tissues, i.e., oxygenated hemoglobin (HbO2) and deoxygenated hemoglobin (HHb) by illuminating the tissue with near infrared (NIR) light and detecting the light that is partially back-scattered by optically-turbid tissues like skin, fat, muscle and bone. Since applying pressure on a slab of tissue significantly affects its hemodynamics by occluding small vessels (capillaries, arterioles and venules), NIRS can measure the effect of such pressure as soon as it manifests [3]. In the last decade, a few studies correlated NIRS-derived tissue oxygenation parameters to PI risk [4], although these were not designed to investigate the disease mechanism. In order to capture hemodynamic events of interest that may relate to the clinical development of PIs, we relied on DOI to 1) measure hemodynamics on a large area of tissue and at different of depths around a bony prominence, and 2) monitor structural features of such hemodynamic changes from the moment pressure is applied and continuously over time.

Methods

Building on the investigator's previous design of a small-sized imaging system for detecting vascular occlusion during surgery [5], the investigators developed a DOI probe embedding 128 emitters (dual-wavelength LEDs at 680 and 780 nm) and 128 detectors (silicon photodiodes) arranged alternatively on a 10-mm regularly-spaced grid (total field of view: 150×150 mm). To follow the curvature of the body (critical for wearability), the probe was built on a flexible printed circuit board (PCB) covered with a layer of optically clear, biocompatible silicone for safe and comfortable application to the human skin. Optical absorption measurements were taken at both wavelengths and in dark condition (LEDs off) to subtract any background contribution. A total of 1,736 optical channels with source-detector separations of 10 mm (480 channels), 22 mm (840 channels) and 30 mm (416 channels) were used to reconstruct tomographic images of changes of $HbO_2$ and HHb with NIRFAST, i.e. a finite-element method often utilized for functional brain imaging [6, 7]. Hemodynamic images were reconstructed for a volume of 168×168×12 mm with a voxel size of 1 $mm^3$.

To assess the quality of optical readings and to conduct a preliminary assessment of hemodynamics in soft tissues exposed to prolonged pressure, the investigators asked five healthy volunteers (four males, age 24.6±4.4 yr., weight 71.2±13.9 kg.) to lay supine on a cushioned bed for two hours, thus matching the time period for body repositioning recommended to avoid PI formation. The optical probe was manually placed on the sacral region with the sacrum prominence located in an approximate central position. Hemodynamic images were collected every minute after the body weight pressure was applied onto the sacral tissues for a total of 120 minutes.

The effect of two-hour body weight pressure on the sacral tissues was assessed in terms of patterns of hemodynamic activity (increase or decrease of $HbO_2$ and/or HHb from baseline) measured over time. The investigators used the Structural SIMilarity (SSIM) index [8] as a measure of similarity between two volumetric hemodynamic images, where SSIM=1 indicates perfectly overlapping activity patterns (e.g., co-located hemodynamically active volumes) while SSIM=0 indicates maximally dissimilar activity patterns (e.g., a hemodynamically active volume in one image co-located to an inactive volume in the second image). For each individual subject, the investigators quantified the similarity of activation volumes, separately for $HbO_2$ and HHb, captured one minute after baseline (i.e., reference image) and every minute after ($HbO_{2\ t=N}$ vs. $HbO_{2\ t=1}$, $HHb_{t=N}$ vs. $HHb_{t=1}$). The investigators also evaluated the similarity over time between activity patterns of different hemoglobin species ($HbO_{2\ t=N}$ vs. $HHb_{t=N}$) within each subject. Across different subjects selected pairwise, the investigators quantified the similarity between hemodynamic patterns within-species measured at the same time during the experiment ($HbO_{2\ sbj=X,\ t=N}$ vs. $HbO_{2\ sbj=Y,\ t=N}$, $HHb_{sbj=X,\ t=N}$ vs. $HHb_{sbj=Y,\ t=N}$). To avoid saturation effects in computing SSIM, all hemodynamic images were normalized to the maximum activation value (either positive or negative) measured over the entire experiment. In addition, we chose to mask the hemodynamic images background (i.e., voxels with less than 10% of peak activation value) to avoid considering spatially overlapping, inactive areas that would have resulted in an overestimation of SSIM. To present these results concisely, the investigators computed the average and standard deviation of SSIM values computed for all comparisons of interests. The average is shown as the black line in each figure discussed below, while the standard deviation as shown as a gray band in each figure.

Results

Figure 9:
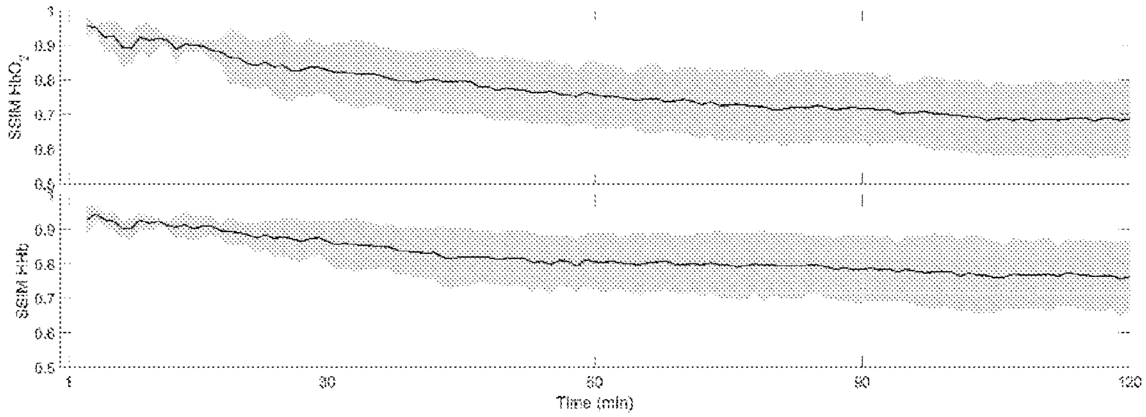
FIG. 9 depicts a graph illustrating the structural similarity index of time-evolving $HbO_2$ (top) and HHb (bottom) images using a subject-specific initial hemodynamic image as reference.

The similarity of hemodynamic changes evaluated over time within each subject is shown in FIG. 9. Expectedly, the SSIM values at the start of the experiment approached unity, as hemodynamic images acquired only few minutes apart were structurally very similar. Subsequently, the average SSIM decreased with the passage of time due to pressure-induced hemodynamic activity that increasingly differed from the initial pattern. Also, the variability of SSIM around the mean value increased over time, reflecting subject-specific downtrend rates.

Figure 10:
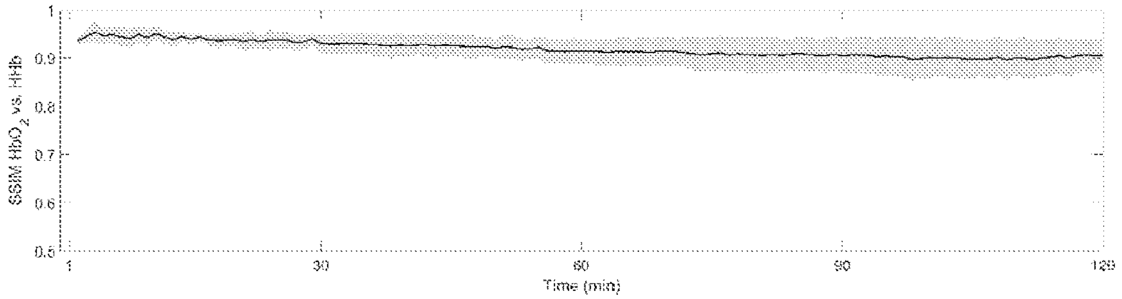
FIG. 10 depicts a graph illustrating the structural similarity index between $HbO_2$ and HHb images acquired simultaneously within a subject

A decreasing SSIM trend was also observed when $HbO_2$ image patterns were compared to HHb patterns within the same individual (FIG. 10). However, similarity across species decreases less compared to similarity within species (FIG. 9), confirming the physiological relation between co-located $HbO_2$ and HHb activities.

Figure 11:
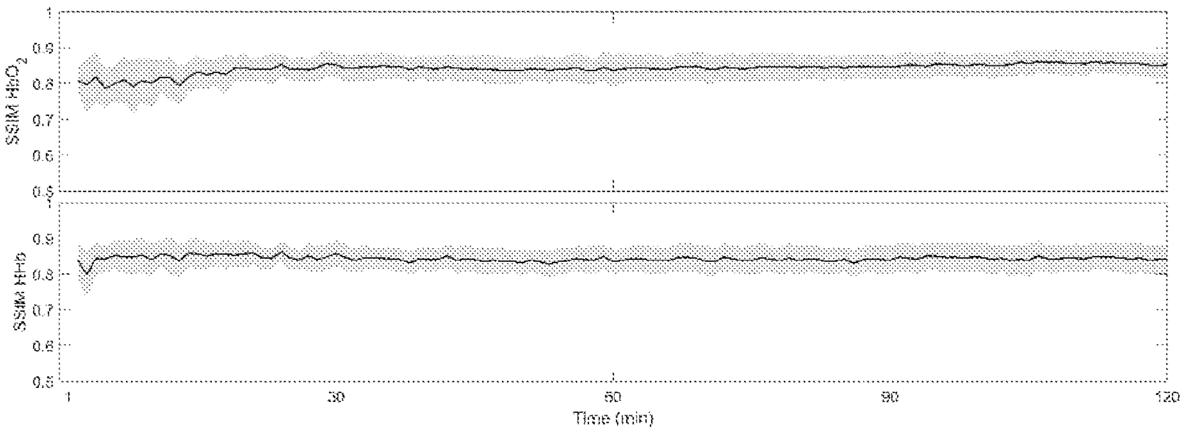
FIG. 11 depicts a graph illustrating the structural similarity index of time-evolving $HbO_2$ (top) and HHb (bottom) images computed across two different subjects.

The hemodynamic similarity computed pairwise across subjects and then averaged is shown in FIG. 11. The initial SSIM value was found to be lower than the corresponding within-subject value due to inter-subject differences between hemodynamic patterns. The mean SSIM for $HbO_2$ slightly increased during the first 30 minutes and reached a plateau thereafter, whereas the SSIM for HHb was essentially constant over time. The SSIM trends also exhibited a limited variability around the mean value, thus denoting a consistent level of image similarity across subjects.

DISCUSSION

To the best of the investigators' knowledge, this is the first study assessing the effect of a prolonged (i.e., 2-hour) body weight pressure on the hemodynamics of sacral tissues minute-by-minute. Although the investigators designed the study around the overarching hypothesis, supported by a strong physiology rationale, that capillary occlusions induced locally by the sacrum pressing onto the interfacing muscle and skin would cause the tissue hemodynamics to change over time, the novelty of the investigators imaging approach made this study partly exploratory in nature, as the measurements of specific patterns of hemodynamic activity were unprecedented. Diffuse optical imaging provides rich information about tissue hemodynamics, i.e. it delivers tomographic images for $HbO_2$ and $HH_b$ concentrations, separately and independently, that may locally increase or decrease as a function of time, making the summarization and interpretation of those images inherently challenging.

To address this matter, the investigators evaluated such complex image features with structural similarity index (SSIM), that is a quantitative measure that reflects, with both fidelity and simplicity, hemodynamics changes over time within the individual subject and also across subjects with different anatomy and physiology.

The results show that, in all subjects, body weight pressure induced hemodynamic changes that began immediately after pressure exertion and continued throughout the 2-hour experiment, thus confirming the overarching hypothesis. This was particularly evident at the individual subject level, where the hemodynamic activity patterns of individual Hb species departed quite substantially from their initial pattern. Still at the subject level, the similarity across-species changed only moderately over time, thus suggesting that, from a hemodynamic imaging perspective, $HbO_2$ and HHb may provide some redundant information about the effect of prolonged pressure. More interestingly, the similarity of hemodynamic pattern across subjects was fairly high and stable over time, which indicates that subjects exhibited consistent image features.

CONCLUSION

This pilot study shows that diffuse optical imaging is a valid tool for investigating hemodynamics effects of prolonged pressure. In the longer term, DOI could elucidate the origination mechanism of PIs and potentially lead to their early detection.

Methods, systems and devices described herein disclose the use NIRS to provide more complete view of oxygenation in a tissue of a bedridden or immobile body to analyze for pressure ulcers. By directing NIRS radiation of a specific wavelength toward a tissue in a multiplexed fashion, the absorbance of a known region and a known wavelength by the tissue can be determined. The detected absorbances are then plotted into a grid. These absorbances directly correlate with the location of HHb and $HbO_2$, thus providing a map of blood flow to the tissue in a near-instantaneous fashion while avoiding user error.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Gould L J, Bohn G, Bryant R, et al (2019) Pressure ulcer summit 2018: An interdisciplinary approach to improve our understanding of the risk of pressure-induced tissue damage, Wound Repair Regen. 2019 September; 27(5): 497-508
2. Gefen, A (2018) The Future of Pressure Ulcer Prevention Is Here: Detecting and Targeting Inflammation Early, EWMA Journal 19: 7-13
3. Jayachandran M, Rodriguez S, Solis E, et al (2016) Critical Review of Noninvasive Optical Technologies for Wound Imaging" Adv Wound Care 5: 349-359
4. Li Z, Zhang M, Wang Y, et al. (2011) Wavelet Analysis of Sacral Tissue Oxygenation Oscillations by Near-Infrared Spectroscopy in Persons with Spinal Cord Injury, Microvasc Res 81: 81-87
5. Pollonini L, Forseth K J, Dacso C C, et al. (2015) Self-Contained Diffuse Optical Imaging System for Real-Time Detection and Localization of Vascular Occlusions, Conf Proc IEEE Eng Med Biol Soc: 5884-5887
6. Dehghani H, Eames M E, Yalavarthy P K, et al (2009) Near infrared optical tomography using NIRFAST: Algorithm for numerical model and image reconstruction. Commun Numer Methods Eng. 2008 Aug. 15; 25(6): 711-732
7. Zeff B W, White B R, Dehghani H, et al (2007) Retinotopic mapping of adult human visual cortex with high-density diffuse optical tomography. Proc Natl Acad Sci USA 104:12169-12174.
8. Simoncelli E P, Sheikh H R, Bovik A C, Wang Z (2004) Image quality assessment: From error visibility to structural similarity. IEEE Trans image Process 13:600-612.
9. U.S. Patent Publication 2015/0164347

The invention claimed is:

1. A device comprising:

a flexible support comprising a first surface, wherein the first surface is configured to be placed in proximity to an epidermis;

a near infrared spectroscopy (NIRS) device comprising:

a plurality of radiation sources coupled to the first surface of the support, wherein the radiation sources are configured to emit a first emitted radiation signal at a first time period and a second emitted radiation signal at a second time period, wherein:

the first emitted radiation signal and the second emitted radiation signal are emitted toward the epidermis when the first surface is placed in proximity to the epidermis; and the second time period is subsequent to the first time period;

a plurality of radiation detectors coupled to the first surface of the support, wherein the radiation detectors are configured to detect a first detected radiation signal at the first time period and a second detected radiation signal at the second time period;

a processor in electronic communication with the radiation detector; and a non-transitory memory adapted to store a plurality of machine-readable instructions which, when executed by the processor, cause the device to:

compare the first detected radiation signal to the second detected radiation signal to calculate a change in an optical property of the epidermis; and determine if the change in the optical property of the epidermis is indicative of a pressure ulcer;

wherein upon placement of each of the plurality of radiation detectors in proximity with the epidermis, each of the plurality of radiation detectors are configured to receive some radiation from each of the radiation sources;

wherein the change in the optical property of the epidermis comprises determining a change in the optical density of the epidermis; and, wherein the device may adjust the first or second emitted radiation signal or the first or second detected radiation signal to account for a pigmentation of the epidermis.

2. The device of claim 1 wherein the plurality of radiation sources are configured to emit a continuous radiation signal that includes the first emitted radiation signal and the second emitted radiation signal.

3. The device of claim 1 wherein the second time period is between 1 second and 100 seconds after the first time period.

4. The device of claim 1 wherein the second time period is between 1 minute and 100 minutes after the first time period.

5. The device of claim 1 wherein the second time period is between 1 hour and 100 hours after the first time period.

6. The device of claim 1 wherein the second time period is between 1 day and 100 days after the first time period.

7. The device of claim 1 wherein:

the plurality of radiation detectors are configured to detect a third detected radiation signal at a third time period; and the plurality of machine-readable instructions, when executed by the processor, cause the device to:

compare the third detected radiation signal to the first detected radiation signal or the second detected radiation signal to calculate a change in an optical property of the epidermis; and determine if the change in the optical property of the epidermis is indicative of a pressure ulcer.

8. The device of claim 7 wherein:

the plurality of radiation detectors are configured to detect a fourth detected radiation signal at a fourth time period; and the plurality of machine-readable instructions, when executed by the processor, cause the device to:

compare the fourth detected radiation signal to the first detected radiation signal, the second detected radiation signal, or the third detected radiation signal to calculate a change in an optical property of the epidermis; and determine if the change in the optical property of the epidermis is indicative of a pressure ulcer.

9. The device of claim 1 wherein the plurality of radiation detectors are a component of a near infrared spectroscopy (NIRS) device.

10. The device of claim 1 wherein the change in the optical property of the epidermis further comprises determining a change in the rate at which the optical density of the epidermis has changed.

11. The device of claim 1 further comprising a temperature sensor, wherein:

the temperature sensor is configured to obtain a first temperature reading at the first time period;

the temperature sensor is configured to obtain a second temperature reading at the second time period; and the plurality of machine-readable instructions includes instructions which, when executed by the processor, cause the device to:

compare the first temperature reading to the second temperature reading to calculate a change in a temperature of the epidermis; and determine if the change in the temperature of the epidermis is indicative of a pressure ulcer.

12. The device of claim 11 wherein the change in the temperature of the epidermis is a change in the rate at which the temperature of the epidermis has changed.

13. The device of claim 1 further comprising a humidity sensor, wherein:

the humidity sensor is configured to obtain a first humidity reading at the first time period;

the humidity sensor is configured to obtain a second humidity reading at the second time period; and the plurality of machine-readable instructions includes instructions which, when executed by the processor, cause the device to:

compare the first humidity reading to the second humidity reading to calculate a change in a humidity of the epidermis; and determine if the change in the humidity of the epidermis is indicative of a pressure ulcer.

14. The device of claim 13 wherein the change in the humidity of the epidermis is a change in the rate at which the humidity of the epidermis has changed.

15. The device of claim 1 wherein the plurality of machine-readable instructions when executed by the processor, cause the device to:

create a volumetric map, the dimensions of the volumetric map corresponding to the tissue portion;

subdivide the volumetric map into volumetric subregions, the volumetric subregions comprising a plurality of voxels, each voxel being assigned one of preassigned values and random values;

create a sensitivity map based on a photon migration pattern;

overlay the sensitivity map onto the volumetric map; and perform at least one iterative cycle, the iterative cycle comprising:

determining the measurement array and the calculated array for the volumetric map, the measurement array comprising optical measurements corresponding to the photon migration pattern, the calculated array comprising determined measurements corresponding to the assigned value as weighted by the photon migration pattern;

increasing an assigned value of a test voxel of the volumetric map, each of the test voxel being selected from the voxels of the volumetric subregions, the increase perturbing the volumetric map;

calculating perturbed determined measurements of a perturbed calculated array for the volumetric map; and determining an error between the measurement array and the perturbed calculated array of the volumetric map, wherein a transformation is applied locally to the test voxel and incorporates the error; and repeat the iterative cycle until one of a preset maximum is reached and the measurement error is less than a present threshold.

16. The device of claim 15 wherein the device further comprises:

a plurality of temperature detectors positioned in connection with the first surface; and the plurality of machine-readable instructions includes instructions which, when executed by the processor, cause the device to create a temperature map, the dimensions of the temperature map corresponding to a thermal dispersion pattern.

17. The device of claim 15 wherein the device further comprises:

a plurality of humidity detectors positioned in connection with the first surface; and the plurality of machine-readable instructions includes instructions which, when executed by the processor, cause the device to create a humidity map, the dimensions of the humidity map corresponding to a fluid vapor amount.

18. The device of claim 15, wherein each voxel is assigned a value determined by a previous set of iterative cycle.

19. The device of claim 15, wherein the plurality of radiation sources are positioned equidistance from the detector.

20. The device of claim 15, wherein the transformation comprises a volumetric Gaussian kernel, wherein if the perturbation causes the error to go down, then the volumetric Gaussian kernel having a radius is centered on the test voxel, the volumetric Gaussian kernel extending to a plurality of proximate voxels, the test voxel and the proximate voxels being permanently increased in value proportionally to the magnitude of the error decrease multiplied by a proportional factor A, and if the perturbation causes the error to go up, then a volumetric Gaussian kernel having a radius is centered on the test voxel, the volumetric Gaussian kernel extending to a plurality of proximate voxels, the test voxel and the proximate voxels being permanently decreased in value proportionally to the magnitude of the error increase multiplied by a proportional factor A.

21. The device of claim 15, wherein at least one of the plurality of radiation sources delivers radiation at a wavelength of about 660 nm.

22. The device of claim 15, wherein at least one of the plurality of radiation sources delivers radiation at a wavelength of about 880 nm.

23. The device of claim 15, wherein the support has an octagonal shape and the radiation sources are configured in concentric circles expanding from a detector in the center of the octagonal shape.

* * * * *